United States Patent
Jordan et al.

(10) Patent No.: US 6,228,794 B1
(45) Date of Patent: May 8, 2001

(54) CATIONIC GROUP 13 COMPLEXES INCORPORATING BIDENTATE LIGANDS AS POLYMERIZATION CATALYSTS

(75) Inventors: Richard F. Jordan, Iowa City, IA (US); Martyn P. Coles, Berkeley, CA (US); Samuel Dagorne; Eiji Ihara, both of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/033,489

(22) Filed: Mar. 3, 1998

Related U.S. Application Data

(63) Continuation-in-part of application No. 08/818,297, filed on Mar. 14, 1997, now Pat. No. 5,777,120.
(60) Provisional application No. 60/068,641, filed on Dec. 23, 1997.

(51) Int. Cl.[7] ............... B01J 31/00; C08F 2/00; C08F 4/00

(52) U.S. Cl. .............. 502/150; 502/152; 502/153; 502/154; 502/155; 502/156; 502/167; 526/89; 526/209; 526/217

(58) Field of Search ................. 502/150, 152, 502/153, 154, 155, 156, 167; 526/89, 209, 217

(56) References Cited

U.S. PATENT DOCUMENTS

| | | |
|---|---|---|
| 2,699,457 | 1/1955 | Ziegler et al. ............ 556/176 |
| 3,373,178 | 3/1968 | Schmidt et al. ........... 556/173 |
| 3,644,224 | 2/1972 | Hani et al. ................ 260/2 A |
| 4,176,090 | 11/1979 | Vaughan et al. ......... 252/455 Z |
| 4,325,885 | 4/1982 | Dozzi et al. ............. 260/448 R |
| 4,434,103 | 2/1984 | Interrante ............... 260/448 B |
| 5,066,741 | 11/1991 | Campbell, Jr. ............ 526/171 |
| 5,235,078 | 8/1993 | Pohl et al. .................. 556/1 |
| 5,318,935 | 6/1994 | Canich et al. ............. 502/117 |
| 5,371,309 | 12/1994 | Moini ....................... 585/407 |
| 5,428,120 | 6/1995 | Newman et al. ........... 526/160 |
| 5,434,115 * | 7/1995 | Yamada et al. ........... 502/155 |
| 5,453,410 | 9/1995 | Kolthammer et al. ...... 502/155 |
| 5,468,707 | 11/1995 | Pohl et al. ................ 502/153 |
| 5,502,128 | 3/1996 | Flores et al. ............. 526/160 |
| 5,527,752 | 6/1996 | Reichle et al. ........... 502/117 |
| 5,561,216 | 10/1996 | Barborak et al. ......... 528/392 |
| 5,707,913 | 1/1998 | Schlund et al. ........... 502/200 |
| 5,777,120 * | 7/1998 | Jordan et al. ............. 546/2 |
| 5,973,088 * | 10/1999 | Jordan et al. ............ 526/189 |

FOREIGN PATENT DOCUMENTS

| | | |
|---|---|---|
| 220 029 | 3/1985 | (DE) ........................ 556/175 |
| 0 493 995 A1 | 7/1992 | (EP) . |
| 4312568 | 11/1992 | (JP) . |
| 5-4957 | 1/1993 | (JP) . |

OTHER PUBLICATIONS

R. Giezynski et al., J. Organomet. Chem., vol. 69, pp. 345–352, 1974.*
J. Klerks et al., J. Organomet. Chem., vol. 181, pp. 271–283, 1979.*
V. Gibson et al., J. Organomet. Chem., vol. 550, pp. 453–456, 1998.*
D. Atwood et al., J. Am. Chem. Soc., vol. 117, No. 25, pp. 6779–6780, 1995.*
M. Coles et al., Organometallics, vol. 16, No. 24, pp. 5183–5194, 1997.*
C–C. Chang et al., Organometallics, vol. 17, No. 8, pp. 1595–1601, 1998.*
S. Aeilts et al., Organometallics, vol. 17, No. 15, pp. 3265–3270, 1998.*
M. Coles et al., Organometallics, vol. 17, No. 18, pp. 4042–4048, 1998.*
K. Dehnicke et al., J. Organomet.Chem.,vol.352,pp.C1–C4, 1988.
M.Wedler et al., J.Organomet.Chem.,vol.388,pp.21–45, 1990.
K.Dehnicke, Chemiker–Zeitung,vol.114,No.10, pp.295–304, Oct. 1990.
J.Buijink et al., Z.Naturforsch.,vol.46b,pp.1328–1332, 1991.
A. Chernega et al., J.Chem.Soc.,Chem.Commun., pp.1415–1417, 1993.
R.Duchateau et al., J.Am.Chem.Soc.,vol.115, pp.4931–4932, 1993.
A. Goodwin et al., Macromolecules,vol.27,pp.5520–5522, 1994.
R. Gomez et al., J.Organomet.Chem.,vol.491, pp.153–158, 1995.
Chemical Abstracts; vol. 118, p.18, 1993, 169853w, Pons, et al., Crosslinked poly(organosilylhydrazine) ceramic . . . .
Chemical Abstracts, vol. 123, p.7, 1995, 84111f, Atwood, et al., Cationic Aluminum Compounds . . . .
Louis M. Woicinski II, et al., The Polymerization of Ethylene and Higher Olefins Using Transition Metal–Free Aluminum Based Catalyst Systems, *Polymer Preprints,* 39, 2, p. 15, 1998.
"Chemistry of Aluminum, Gallium, Indium, and Thallium", A.J. Downs, Ed.; Blackie Academic & Professional, Chapan & Hall, Glasgow, 1993, pp. 322–371.

(List continued on next page.)

*Primary Examiner*—Mark L. Bell
*Assistant Examiner*—J. Pasterczyk
(74) *Attorney, Agent, or Firm*—Morgan, Lewis & Bockius LLP

(57) ABSTRACT

Disclosed are novel catalysts, processes of synthesizing the catalysts and to olefin polymerization processes using the catalysts. The catalysts are cationic complexes comprising a Group 13 element and certain ligands. These compounds behave similarly to Ziegler-Natta catalysts but effectively catalyze the polymerization of olefins in the absence of any transition metal.

42 Claims, No Drawings

OTHER PUBLICATIONS

Steven H. Strauss, Chemical Reviews, "The Search for Larger and More Weakly Coordinating Anions", vol. 93, No. 3, 1993, pp. 927–942.

H. Martin and H. Britinger, "High–molecular–weight polyethylene: growth reactions at bis(dischloraluminum)ethane and trialkylaluminum," Macromolecular Chemistry and Physics, vol. 193, 1992, pp. 1283–1288.

R. H. Crabtree, "Transistion Metal Complexation of σ Bonds", Angew, Chemie Int. Ed. Engl., vol. 32, 1993, pp. 789–805.

H. Schmidbaur, G. Kuhr, and U. Kruger, "Organometallic Derivatives of Iminotriphenylphosphorane," Angew. Chem. Int. Ed. Engl., vol. 4, No. 10, 1965, p. 877.

Jerald Feldman et al., "Electrophilic Metal Precursors and a β–Diimine Ligand for Nickel(II)–and Palladium(II)–Catalyzed Ethylene Polymerization", Organometallics, vol. 16, 1997, pp. 1514–1516.

H. V. Rasika Dias et al., "Aluminum Derivatives of N–Isopropyl–2–(isopropylamino)troponimine", Inorganic Chemistry, vol. 34, 1995, pp. 6100–6105.

Hermann Stettr and Claus Wulff, "Derivate de 1–Amino–adamantans", Chemische Berichte, Apr. 1962, pp. 2302–2304.

* cited by examiner

CATIONIC GROUP 13 COMPLEXES INCORPORATING BIDENTATE LIGANDS AS POLYMERIZATION CATALYSTS

CROSS-REFERENCE TO RELATED APPLICATIONS

This application is a continuation-in-part of U.S. application Ser. No. 08/818,297 filed Mar. 14, 1997 and entitled CATIONIC ALUMINUM ALKYL COMPLEXES INCORPORATING AMIDINATE LIGANDS AS POLYMERIZATION CATALYSTS now U.S. Pat. No. 5,777,120, and claims the benefit of U.S. Provisional Application Ser. No. 60/068,641 filed Dec. 23, 1997 and entitled CATIONIC GROUP 13 COMPLEXES INCORPORATING BIDENTATE LIGANDS AS POLYMERIZATION CATALYSTS.

BACKGROUND OF THE INVENTION

Ziegler-Natta type catalysts for polymerization of unsaturated hydrocarbons, such as alpha olefins, have long been the state of the art catalysts for such reactions. Typically, Ziegler-Natta type catalysts are composed of transition metal salts and aluminum alkyl compounds, e.g., titanium tetrachloride and triethylaluminum. While these catalysts are very effective and have a long-established record of use, they are not without drawbacks. For example, transition metals are expensive, potentially present some toxicity hazards, and to some are environmentally objectionable. Therefore, efforts towards the development of alternative, suitable olefin polymerization catalysts have occurred. For example, metallocene catalysts have been developed for use in alpha olefin polymerization. The polymerization of ethylene using an aluminum-based catalyst but in the absence of a transition metal is known. For example, the formation of polyethylene by the polymerization of ethylene in the presence of catalysts prepared by the reaction of neutral aluminum compounds, such as $Cl_2AlCH(Me)AlCl_2$ or $(AlR_3)_2$, with ethylene at a temperature in the range of 25 to 50° C. has been reported by H. Martin and H. Bretinger, *Makromol. Chem.* 1992, 193, 1283. However, the reported catalytic activities are very low ($1.6 \times 10^{-1}$–$3.8 \times 10^{-4}$ g PE/(mol*h*atm)).

The present invention has as its primary objective the development of more highly active catalysts useful for the polymerization of unsaturated hydrocarbons which do not require a transition metal compound as a component of the catalyst.

Another objective of the present invention is to prepare such catalysts in high yields using convenient and practical synthetic methods.

A yet further objective of the present invention is a method for polymerizing unsaturated hydrocarbons using the novel, transition metal-free catalysts provided by this invention.

The method and manner of accomplishing each of the above objectives, as well as others, will become apparent from the detailed description of the invention which follows hereinafter.

SUMMARY OF THE INVENTION

This invention relates to novel catalysts, processes of synthesizing the catalysts and to olefin polymerization processes using the catalysts. The catalysts are cationic complexes comprising a Group 13 element and certain ligands. These compounds behave similarly to Ziegler-Natta catalysts but effectively catalyze the polymerization of olefins in the absence of any transition metal.

DETAILED DESCRIPTION OF THE INVENTION

We have discovered that the compositions defined below are effective catalysts for the polymerization of olefins. Therefore, one embodiment of the present invention is represented by a catalyst composition comprising components (1), (2) and (3) wherein component (1) is a Lewis acid having the formula:

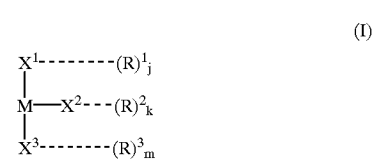

(I)

wherein

M is an atom selected from the Group 13 elements, i.e., a boron, aluminum, gallium, indium or thallium atom;

$X^1$, $X^2$ and $X^3$ are the same or different and each is selected from hydrogen and the elements of Groups 14, 15, 16 and 17;

$R^1$, $R^2$ and $R^3$ are the same or different and each is selected from hydrogen, hydrocarbyl, substituted hydrocarbyl, nitrogen or oxygen-containing heterocyclic, silyl, siloxy groups or metallic groups such as Al(III), Mg(II) and two groups ($R^1$, $R^2$ or $R^3$) may be combined to form with $X^1$, $X^2$, or $X^3$ a cyclic group; and j, k and m are the same or different and may be 0, 1, 2 or 3 as required to satisfy the valence of each of atoms $X^1$, $X^2$ and $X^3$ to which $R^1$, $R^2$ and $R^3$, respectively, are bound;

component (2) is a Lewis-base having the formula $E(R^4)_n$ wherein E is an atom selected from the Group 15 and 16 elements; $R^4$ represents up to 3 substituents which may be the same or different and are selected from hydrogen, hydrocarbyl, substituted hydrocarbyl, silyl, alkoxy, aryloxy and amino; n is 1, 2 or 3 as required to satisfy the valence of E to which $R^4$ is bound; and two groups, $R^4$, may be attached so as to form a cyclic structure as found in tetrahydrofuran (E=O, $(R^4)_2$=$(CH_2)_4$) or pyridine (E=N, $(R^4)_2$=$(CH)_5$); and component (3) is an activator selected from (a) a salt of a labile, non-coordinating or weakly coordinating anion that is capable of replacing one of the —$X^1$—$(R^1)_j$, —$X^2$—$(R_2)_k$ or —$X^3$—$(R^3)_m$ groups of component (1); (b) a neutral Lewis-acid that is capable of abstracting one of the —$X^1$—$(R^1)_j$, —$X_2$—$(R^2)_k$ or —$X^3$—$(R^3)_m$ groups from component (1); (c) an oxidizing agent capable of reacting with component (1) and converting it to a cationic derivative; and (d) alumoxanes.

The hydrocarbyl group which $R^1$, $R^2$, $R^3$ and/or $R^4$ may represent may be a saturated or unsaturated, unsubstituted or substituted, aliphatic, alicyclic, heterocyclic or aromatic group containing up to about 50 carbon atoms, preferably up to about 12 carbon atoms. Examples of the substituents which may be present on the substituted hydrocarbyl groups include methyl, ethyl, isopropyl, isobutyl, t-butyl, neopentyl, alkoxy, and halogen. Examples of the aromatic groups which $R^1$, $R^2$, $R^3$ and/or $R^4$ may represent include, phenyl, naphthyl, and anthracenyl with substituents selected from methyl, ethyl, isopropyl, t-butyl, silyl, aryl, alkoxy, amino, or a halogen. The alkoxy or amino groups which $R^1$, R², R³ and/or R⁴ may represent may contain up to about 50 carbon atoms, preferably up to about 12 carbon atoms.

Examples of the groups represented collectively by —X¹—(R¹)ⱼ, —X²—(R²)ₖ and —X³—(R³)ₘ include methoxy, ethoxy, isopropoxy, t-butoxy, phenoxy, thiophenoxy, N-methylanilino, diisopropylamino, bis(trimethylsilyl)amino, dimethylphosphido, dicyclohexylphophido, diphenylphosphido, pivalate, N,N'-diisopropylacetamidinate, N,N'-dicyclohexylacetamidinate, N,N'-diadamantylacetamidinate, N,N'-bis(2,6-dimethylphenyl)acetamidinate, N,N'-diisopropylpivamidinate, N,N'-dicyclohexylpivamidinate, N,N'-diadamantylpivamidinate, N,N'-bis(2,6-dimethylphenyl)pivamidinate, t-butyl-N-isopropylcarbamate, t-butyl-N-isopropylthiocarbamate, diisopropyldithiocarbamate, N,N-dimethyl-N',N''-diisopropylguanadinate, N,N-diethyl-N',N''-diisopropylguanadinate, N,N-diisopropyl-N',N''-diisopropylguanadinate, N,N-bis(trimethylsilyl)-N',N''-diisopropylguanadinate, 1,3,4,6,7,8-hexahydro-2H-pyrimido[1,2-a]pyrimidinate, thiopivalate, dithiopivalate, N,N'-diadamantylthioureate, N,N'-bis(2,6-dimethylphenyl)thioureate, N,N'-bis(2,6-diisopropylphenyl)thioureate, and N,N'-bis(t-butyl)thioureate. The groups represented collectively by —X¹—(R¹)ⱼ, —X²—(R²)ₖ and —X³—(R³)ₘ preferably are selected from N,N'-diisopropylacetamidinate, N,N'-dicyclohexylacetamidinate, N,N'-diadamantylacetamidinate, N,N'-diisopropylpivamidinate, N,N'-dicyclohexylpivamidinate, N,N'-diadamantylpivamidinate, N,N-dimethyl-N',N''-diisopropylguanadinate, N,N-diethyl-N',N''-diisopropylguanadinate, N,N'-diadamantylthioureate.

The most preferred groups represented by —X¹—(R¹)ⱼ, —X²—(R²)ₖ and —X3—(R³)ₘ are N,N'-diisopropylpivamidinate, N,N'-dicyclohexylpivamidinate, N,N'-bis(adamantyl)pivamidinate.

Examples of the Lewis-base compounds represented by E(R⁴)ₙ include dimethyl ether, tetrahydrofuran, methyl-t-butylether, dimethylsulfide, trimethylamine, triethylamine, tributylamine, 2,6-lutidine, 2,4,6-collidine, N,N-dimethylaniline, 2,6-diisopropylaniline, trimethylphosphine, triethylphosphine, tricyclohexylphosphine, triphenylphosphine, and triphenylphosphite. The Lewis-base is utilized in the range of 0 to 1000 molar equivalents relative to Component (1) with a minimum being preferred to minimize the competitive inhibition of polymerization. The Lewis-base compound represented by E(R⁴)ₙ preferably is selected from methyl-t-butylether, 2,6-lutidine, 2,4,6-collidine, N,N-dimethylaniline and 2,6-diisopropylaniline.

Examples of the component (3) activators include (1) salts of labile, non-coordinating or weakly coordinating anions that are capable of abstracting one of the —X¹—(R¹)ⱼ, —X²—(R²)ₖ or —X³—(R³)ₘ groups from component (1) such as the alkali metal, silver, thallium, triphenylcarbenium, or anilinium salts of tetraphenylborate, tetrakis(pentafluorophenyl)borate; tetrakis[3,5-bis(trifluoromethyl)phenyl]borate, tetrafluoroborate, hexafluorophosphate, hexafluoroantimonate, perchlorate, trifluoromethanesulfonate, nonafluorobutylsulfonate, $(B_{12}H_{12})^{2-}$, $(CB_{11}H_{12})^{-}$, $(C_2B_9H_{12})^{-}$, or $[(C_2B_9H_{11})_2Co]^{-}$; (2) neutral Lewis acids that are capable of abstracting one of the —X¹—(R¹)ⱼ, —X²—(R²)ₖ or —X³—(R³)ₘ groups from component (1) such as triphenylboron, tris(pentafluorophenyl)boron; tris[3,5-bis(trifluoromethyl) phenyl]boron, trialkylaluminum, and alumoxanes; (3) oxidizing agents capable of reacting with component (1) and converting it to a cationic derivative such as ferrocenium or silver salts of non-coordinating or weakly coordinating anions. These are typically applied in a molar ratio of Components (1):(3) from 1:0.001–100,000.

The activator alumoxanes are well known in the art and comprise oligomeric linear and/or cyclic alkyl alumoxanes represented by the formula:

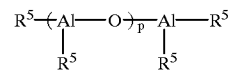

for oligomeric, linear alumoxanes and:

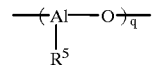

for oligomeric, cyclic alumoxane, wherein p is 1–40, preferably 10–20, q is 3–40, preferably 3–20, and R⁵ is an alkyl group of up to about 8 carbon atoms, preferably methyl. Generally, in the preparation of alumoxanes from, for example, trimethylaluminum and water, a mixture of linear and cyclic compounds is obtained.

The component (3) activator preferably is selected from tris(perfluorophenyl)boron, triphenylcarbenium [tetrakis(perfluorophenyl)borate], and alumoxanes and is preferably applied in a molar ratio of component (1):(3) of 1:0.1–1,000. Use of an excess of (3) is advantageous as a scavenger of surreptitious impurities.

Another embodiment of the present invention is a two-component catalyst composition comprising components (3), as described above, and (4), defined as a complex of a Group 13 metal having the formula:

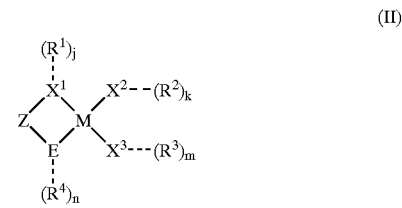

(II)

wherein M, X¹, X², X³, E, R¹, R², R³, R⁴, j, k, m and n are defined above and Z is a saturated or unsaturated linking group, e.g., a methylene or methylidene group or a chain of 2 to 30 carbon atoms or 2 to 12 atoms comprising carbon and a second element selected from oxygen, sulfur or nitrogen. Examples of the linking groups represented by Z include ethylene, propylene, butylene, trimethylene, a group having the formula =CHCH=CH—, or aminomethylidene, which has the formula:

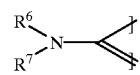

wherein R⁶ and R⁷ are the same or different and each is selected from hydrogen, hydrocarbyl, substituted hydrocarbyl or silyl groups. Groups R⁶ and R⁷ may form a cyclic moiety if a covalent network creates a second link between the bridge, Z, and atoms X¹ or E. Pyrimidinates illustrate such structures:

amino-pyrimidinate: 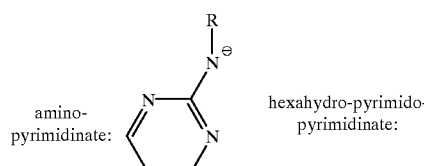   hexahydro-pyrimido-pyrimidinate: 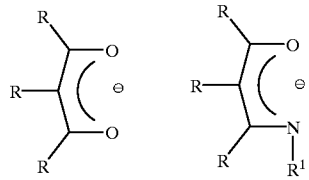

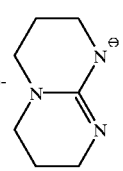 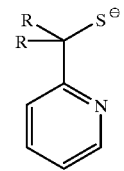

Examples of the residues represented by

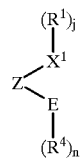

include residues in which Z is a bridging group having the structure:

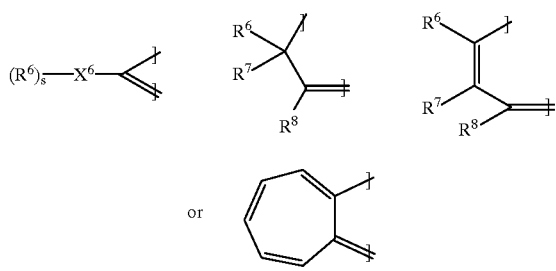

or wherein $R^6$, $R^7$ and $R^8$ are the same or different and each is selected from hydrogen, a hydrocarbyl group and a silyl group; $X^6$ is an oxygen, nitrogen, carbon or silicon atom; and s is 1, 2, or 3 as required to satisfy the valence of $X^6$. The following formulas depict examples of residues which may be represented by $(R^1)_j X^1$—Z—$E(R^4)_n$.

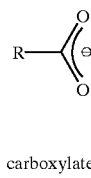 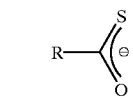 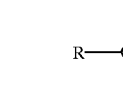 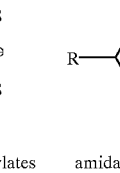

carboxylates    thiocarboxylates    dithiocarboxylates    amidates

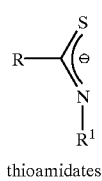 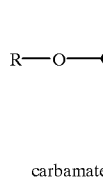 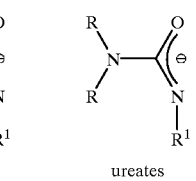

thioamidates    carbamates    ureates

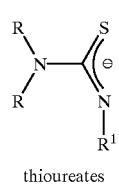 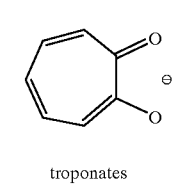

thioureates    troponates

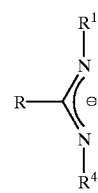 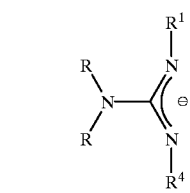 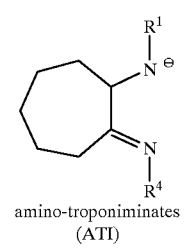

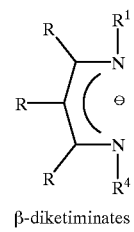 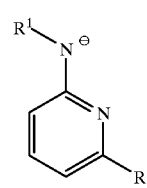 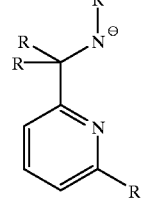

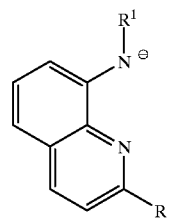

In the formulas, R indicates a generic substituent while $R^1$ is bound to $X^1$.

Residues in which both $X^1$ and E are nitrogen atoms, j and n=1, and $R^1$ and $R^4$ are alkyl, aryl, or silyl groups are preferred (see the formulas set out below).

In addition, groups $R^1$ and $R^4$ that impart a steric encumbrance to the coordination sphere of the metal ligated to $X^1$ and E are further preferred. Examples of the latter include alkyl groups bound to $X^1$ or E by secondary or tertiary carbons such as isopropyl, cycylohexyl, t-butyl, and adamantyl; aryl groups with substitution in the ortho position such as 2,6-dimethylphenyl and 2,6-diisopropylphenyl; and trisubstituted silyl groups such as trimethylsilyl. Other examples will be apparent to those skilled in the art.

amidinates    guanidates    amino-troponiminates (ATI)

β-diketiminates

The formulas shown above are examples of preferred residues, $(R^1)_j X^1$—Z—$E(R^4)_n$. $R^1$ is bound to $X^1$, $R^4$ to E, and R is a generic substituent.

In cases where the bridging group Z is unsaturated the anionic residues represented by

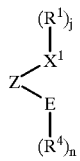

may be depicted by the resonance hybrid of their localized resonance structures. For example, the amidinate ligands may be represented by structure C, which is the resonance hybrid of localized resonance structures A and B. Similarly, the aminotroponiminate ligand may be depicted as structure F, which is the resonance hybrid of D and E (shown below) and the base-free cationic aluminum amidinate complexes may be represented by structure J, which is the resonance hybrid of localized resonance structures G and H.

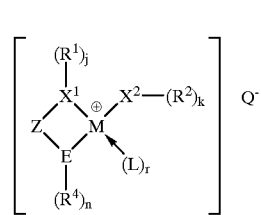

wherein M, $X^1$, $X^2$, $R^1$, $R^2$, $R^4$, j, k, n, E and Z are defined above, L is a neutral Lewis base or a donor ligand, r is 0–3, and $Q^-$ is a non-coordinating or weakly coordinating anionic group. L, the optional neutral Lewis base, is conventional and well known. Examples of neutral Lewis bases which L represents include an aliphatic or cyclic ether such as a dialkyl ether containing 2 to about 12 carbon atoms (e.g.,

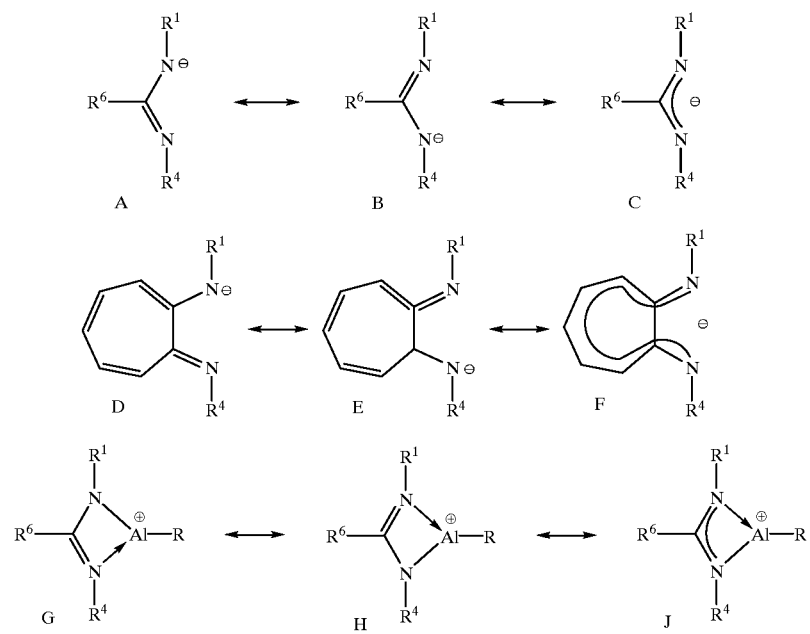

A preferred embodiment of the complexes of formula (II) are aluminum amidinate compounds having the formula:

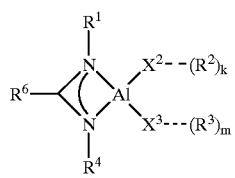

wherein $R^1$, $R^4$, and $R^6$ are selected from the groups consisting of $C_1$ to $C_{50}$ alkyl, aryl or silyl, such as methyl, ethyl, i-propyl, t-butyl, cyclohexyl, adamantyl, phenyl, 2,6-dimethylphenyl, 2,6-diisopropylphenyl, 2-t-butylphenyl and $-X^2-(R^2)_k$ and $-X^3-(R^3)_m$ are selected from the groups consisting of hydrogen, methyl, ethyl, isobutyl, neopentyl, benzyl, phenyl, or halogen.

A third embodiment of the present invention comprises a single-component catalyst having the formula:

tetrahydrofuran), pyridines(e.g., lutidine), and phosphines (e.g., tricyclohexylphosphine). L also may be a species which can act as a donor to the cationic Group 13 metal though coordination of a π-bond, (e.g., benzene or toluene) or even a σ-bond (e.g., H-SiEt$_3$). Examples of such novel σ-donors are well-known and have been reviewed (see Crabtree, R. H.; *Ang. Chem., Intl. Ed. Engl.,* 1993, 32, 789–805). L also may be a neutral or cationic Group 13 metal species such as [MeC(N$^i$Pr)$_2$]AlMe$_2$, AlMe$_3$, AlCl$_3$ or [[MeC(N$^i$Pr)$_2$]AlMe]$^+$ which coordinates to the cation through a bridging group. In the latter case, dimeric dicationic species can result such as that depicted below (related oliogmers are readily envisioned).

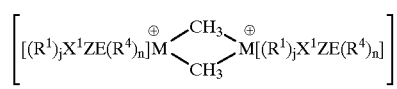

The presence of such neutral coordinating ligands L is not critical, and they may and may not be present as deemed appropriate in any particular reaction.

The Q⁻ moiety represents the non-coordinating or weakly coordinating counterbalancing anion. In particular, it represents a compatible, non-coordinating anion containing a single coordination complex comprising a charge-bearing metal or metalloid core which is relatively large (bulky), capable of stabilizing the active catalyst species and being sufficiently labile to be displaced by olefinic, diolefinic or acetylenically unsaturated substrates, or other neutral Lewis bases or donor groups, such as ethers, nitriles and the like. Polyhedral borane anions, carborane anions and metallocarborane anions are also useful non-coordinating or weakly coordinating counterbalancing anions.

The key to proper anion design requires that the anionic complex is labile and stable toward reactions in the final catalyst species. Anions which are stable toward reactions with water or Bronsted acids and which do not have acidic protons located on the exterior of the anion (i.e. anionic complexes which do not react with strong acids or bases) possess the stability necessary to qualify as a stable anion for the catalyst system. The properties of the anion which are important for maximum lability include overall size, and shape (i.e. large radius of curvature), and nucleophilicity.

Using these guidelines one can use the chemical literature to choose non-coordinating anions which can serve as components in the catalyst system. In general, suitable anions for the second component may be any stable and bulky anionic complex having the following molecular attributes: (1) the anion should have a molecular diameter about or greater than 4 angstroms; (2) the anion should form stable salts with reducible Lewis Acids and protonated Lewis bases; (3) the negative charge on the anion should be delocalized over the framework of the anion or be localized within the core of the anion; (4) the anion should be a relatively poor nucleophile; and (5) the anion should not be a powerful reducing or oxidizing agent. Anions meeting these criteria, e.g., polynuclear boranes, carboranes, metallacarboranes, polyoxoanions and anionic coordination complexes, are well described in the chemical literature.

Illustrative, but not limiting examples of non-coordinating or weakly coordinating counterbalancing anions represented by Q⁻, are tetra(phenyl)borate, tetra(p-tolyl)borate, tetra (pentafluorophenyl)borate, tetra(3,5-bis-trifluoromethyl-phenyl)borate, $C_2B_9H_{12}^-$, $CB_{11}H_{12}^-$, $B_{12}H_{12}^{2-}$, and $(C_2B_9H_{11})_2Co^-$. Triarylborates such as methyl[tris(pentafluorophenyl)]borate and methyl(tris[3,5-bis(trifluoromethyl)phenyl])borate are also weakly coordinating anions formed by the abstraction of a methyl group from a Group 13 metal by the neutral triarylboron derivatives. Related derivatives in which one group on a boron- or aluminumate anion (Q⁻) is derived from a Group 13 catalyst percursor by an abstraction reaction with a boron or aluminum Lewis acid can be envisioned. For instance, the reaction of methyl-alumoxane with dimethylaluminum-(N,N'-diisopropylpivamidinate) may yield a reactive cationic aluminum catalyst associated with a methylalumoxanate anion.

As earlier stated, generally, these anions are labile and can be displaced by an olefin, di-olefin or acetylenically unsaturated monomer, have a molecular diameter about or greater than 4 angstroms, form stable salts with reducible Lewis acids and protonated Lewis bases, have a negative charge delocalized over the framework on the anion of which the core thereof is not a reducing or oxidizing agent, and are relatively poor nucleophiles. For other examples of counterbalancing, non-coordinating or weakly coordinating anions, see Strauss, S. H.; *Chemical Reviews*, 1993, 93, 927–942.

Q⁻ preferably represents tetrakis(pentafluorophenyl) boronate or tetrakis[bis(3,5-trifluoromethylphenyl)] boronate.

A preferred embodiment of the complexes of formula (III) are aluminum amidinate compounds having the formula:

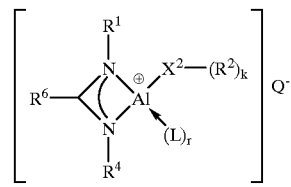

wherein $R^1$, $R^4$, and $R^6$ are selected from the group consisting of $C_1$ to $C_{50}$ alkyl, aryl or silyl, $-X^2-(R^2)_k$ is selected from the group consisting of hydrogen, chloride, methyl, ethyl, isobutyl, neopentyl, and benzyl; L is a labile Lewis base or donor ligand or a neutral or cationic aluminum species capable of coordination; and Q⁻ is a counterbalancing non-coordinating or weakly coordinating anion.

The cationic Group 13 complexes may be prepared by reacting a neutral precursor complex of the type $[(R^1)_jX-Z-E(R^4)_n]M[X^2(R^2)_k][X^3(R^3)_m]$, where M, $R^1$, $R^2$, $R^3$, $R^4$, $X^2$, $X^3$, k, m, n, and j are as defined above, with an activator capable of abstracting an $-X^3-(R^3)_m$ group from the precursor complex or of cleaving one $M-X^3$ bond of the precursor complex. Suitable activators are those described as component (3) activators in the first and second embodiments above. The syntheses of these catalyst compounds is particularly straightforward and ideally carried out using a high vacuum line and inert atmosphere techniques in the presence of solvents, as presented in the examples. These are illustrative and not intended to be limiting of the invention.

The novel catalyst compositions disclosed herein are useful in effecting the polymerization of unsaturated compounds such as α-olefins, cyclic olefins, dienes, alkynes, and vinyl aromatic monomers. Preferred monomers are α-olefins containing from 2 to about 8 carbon atoms. Homopolymers preferably are prepared from a $C_2$–$C_8$ α-olefin. Copolymers preferably are produced from ethylene and a $C_3$–$C_8$ α-olefin, or propylene and ethylene or another $C_4$–$C_8$ α-olefin. Terpolymers preferably are produced from ethylene and/or propylene and 1 or 2 other $C_2$–$C_8$ α-olefins.

Polymerizations may be conducted by solution, slurry or gas-phase techniques, generally at a temperature in the range of about 0 to 160° C. or even higher, and under atmospheric, subatmospheric or superatmospheric pressure conditions. Conventional polymerization adjuvants such as hydrogen may be employed if desired. It is generally preferred to use the catalyst compositions at a concentration such as to provide about 0.00001 to 0.05 weight percent, most preferably about 0.0001 to 0.005 weight percent of Group 13 metal catalyst.

A solution polymerization process can utilize sub- or super-atmospheric pressure and temperatures in the range of about 40 to 150° C. Catalyst precursor, co-catalysts, and polymerization additives are dissolved in a liquid medium to which ethylene and/or another unsaturated monomer, and hydrogen are added. The liquid employed as polymerization medium can be an inert alkane or cycloalkane, such as butane, pentane, hexane or cyclohexane, or an inert, aromatic hydrocarbon, such as toluene, ethylbenzene or xylene. The medium employed should be liquid under the conditions of the polymerization and relatively inert. Preferably, hexane or toluene is employed.

A slurry polymerization process is practiced under similar conditions of pressure and temperature with a suspension of solid, particulate polymer formed in the polymerization medium to which ethylene and/or another unsaturated monomer, hydrogen and catalyst are added. The liquids employed are similar to those referred to above for solution polymerization with hexane or toluene typically preferred.

Both solution and slurry polymerization may be performed in a bulk phase where the monomer serves as the liquid reaction medium.

Gas-phase polymerization processes utilize superatmospheric pressure and temperature in the range of about 50 to 120° C. Gas-phase polymerization can be performed in a stirred or fluidized bed of catalyst and product particles in a pressure vessel adapted to permit the separation of product particles from unreacted gases. It may be advantageous to use a supported catalyst prepared by depositing catalyst and co-catalyst components on a support material such as alumina, silica, or magnesium chloride. Thermostated ethylene, comonomer, hydrogen and an inert diluent gas such as nitrogen can be introduced or recirculated so as to maintain the particles at a temperature of 50 to 120° C. Trialkylaluminum may be added as needed as scavenger of water, oxygen and other adventitious impurities. Polymer product can be withdrawn continuously or semicontinuously at a rate such as to maintain a constant product inventory in the reactor. After polymerization and deactivation of the catalyst, the product polymer can be recovered by any suitable means. In commercial practice, the polymer product can be recovered directly from the gas phase reactor, freed of residual monomer with a nitrogen purge, and used with or without further deactivation or catalyst removal. The polymer obtained can be extruded into water and cut into pellets or other suitable comminuted shapes. Pigments, antioxidants and other additives, as is known in the art, may be added to the polymer.

The molecular weight of the polymer products obtained from the polymerization processes using the novel catalyst compositions can vary over a wide range, such as low as 500 up to 2,000,000 grams per mole or higher, preferably about 1,000 to 500,000 grams per mole. It is highly desirable to have for many applications, such as extrusion and molding processes, polyethylenes which have a broad molecular weight distribution of the unimodal and/or the multimodal type. Such polyethylenes exhibit excellent processability, i.e., they can be processed at a faster throughput rate with lower energy requirements and at the same time such polymers would evidence reduced melt flow perturbations.

EXAMPLES

In the following examples all procedures were performed on a high-vacuum line or in a glove box under a purified $N_2$ atmosphere. Solvents were distilled from Na/benzophenone ketyl, except for chlorinated solvents, which were distilled from activated molecular sieves (3 Å) or $CaH_2$.

N-isopropyl-2-(isopropylamino)troponimine $\{(^iPr)_2ATI\}H)$, $(AdNH)_2C=S$ (Ad=adamantyl), $(ArNH)_2C=S$ (Ar=2,6-$^iPrC_6H_3$), AdN=C=NAd, ArN=C=NAr, $HC(CMeNAr)_2H$, and $Li[^tBuC(N^iPr)_2]$ and $Li[^tBuC(NCy)_2]$, were prepared by literature methods, see Dias, H. V. R.; Jin, W.; Ratcliff, R. E. *Inorg. Chem.* 1995, 34, 6100; Stetter, H.; Wulff, C. *Chem. Ber.*1962, 95,2302; Ogawa, K; Akazawa, M. Japanese Pat. Appl. JP 91–164070 910410; Ogawa, K; Akazawa, M. Japanese Pat. Appl. JP 91–208987 910517; Feldman, J.; McLain, S. J.; Parthasarathy, A.; Marshall, W. J.; Calabrese, J. C.; Arthur, S. D. *Organometallics* 1997, 16, 1514; Coles, M. P.; Swenson, D. C.; Jordan, R.

F.; Young Jr., V. A. *Organometallics* 1997, 16, 5183, which are incorporated by reference.

$HC(CMeNAr')_2H(Ar'=2-^tBuC_6H_4)$ and $HC(CMeN^tBu)(CMeO)H$ were prepared in an analogous fashion to $HC(CMeNAr)_2H$ using 2-$^tBuC_6H_4NH_2$ and $^tBuNH_2$ respectively.

NMR spectra were recorded on a Bruker AMX 360 spectrometer in sealed or Teflon-valved tubes at ambient probe temperature unless otherwise indicated. $^1H$ and $^{13}C$ chemical shifts are reported versus $SiMe_4$ and were determined by reference to the residual $^1H$ and $^{13}C$ solvent peaks. Coupling constants are reported in Hz. $^{13}C$ NMR spectra of ionic compounds containing $B(C_6F_5)_4$-counterions also contain anion resonances which are not listed in some cases: δ 149 (d, $^1J_{CF}$=242), 139(d, $^1J_{CF}$=246), 137(d,$^1J_{CF}$=246), 125 (br, ipso-B $(C_6F_5)_4$—).

Mass spectra were obtained using the Direct Insertion Probe (DIP) method, on a VG Analytical Trio I instrument operating at 70 eV. Elemental analyses were performed by Desert Analytics Laboratory.

Example 1

$\{MeC(N^iPr)_2\}AlMe_2$. A solution of 1,3-diisopropylcarbodiimide (2.00 g, 10.7 mmol) in hexane (25 mL) was added dropwise via pipette to a rapidly stirred solution of $AlMe_3$ (1.06 mL, 11.0 mmol) in hexane (10 mL). An exothermic reactions was observed. The reaction mixture was stirred at room temperature for 18 h, after which time the volatiles were removed under vacuum affording pure $\{MeC(N^iPr)_2\}AlMe_2$ as a pale yellow liquid (2.30 g, 71%). $^1H$ NMR ($CD_2Cl_2$): δ 3.50 (sept,$^3J_{HH}$=6.3Hz, 2H, $CHMe_2$), 1.94 (s, 3H, CMe), 1.05 (d,$^3J_{HH}$=6.1Hz, 12H, $CHMe_2$),-0.82 (s, 6H, $AlMe_2$). $^{13}C$ NMR ($CD_2Cl_2$): δ172.5 (s, CMe), 45.3 (d,$^1J_{CH=}$132.2 Hz, $CHMe_2$), 25.3 (q, $^1J_{CH}$=125.6 Hz, $CHMe_2$), 11.1 (q,$^1J_{CH}$=128.3 Hz, CMe),-9.94 (br q, $^1J_{CH}$=114.1 Hz, $AlMe_2$). Anal. Calcd for $C_{10}H_{23}N_2Al$: C, 60.57; H, 11.69; N, 14.13. Found: C, 60.41; H, 11.96; N, 14.50.

Example 2

$\{MeC(NCy)_2\}AlMe_2$. A solution of 1,3-dicyclohexylcarbodiimide (5.00 g, 24.2 mmol) in hexane (40 mL) was added slowly to a solution of $AlMe_3$(2.40 mL, 25.0 mmol) in hexane (15 mL). The solution was stirred for 15 h and the volatiles were removed under vacuum yielding a pale yellow liquid that crystallized upon standing to afford pure $\{MeC(NCy)_2\}AlMe_2$ as off-white crystals. (6.49 g, 93%). $^1H$ NMR ($CD_2Cl_2$): δ 3.10 (m, 2H, Cy), 1.92 (s, 3H, CMe), 1.69 (m,8H,Cy),1.56(m,2H,Cy), 1.35-1.06(m,8H+ 2H,Cy), -0.82(s,6H,$AlMe_2$). $^{13}C$ NMR ($CD_2Cl_2$): δ 172.4 (s,CMe), 53.0(d,$^1J_{CH}$=131.4 Hz,Cy—$C_1$), 36.0(t,$^1J_{CH}$=126.5 Hz,Cy), 26.1 (t,$^1J_{CH}$=125.8 Hz,Cy), 25.4 (t,$^1J_{CH}$=126.9 Hz,Cy), 11.2 (q,$^1J_{CH}$=128.0 Hz, CMe),-9.78 (br q),$^1J_{CH}$=112.6 Hz, $AlMe_2$). Anal. Calcd for $C_{16}H_{31}N_2Al$: C, 69.02; H, 11.22; N, 10.06. Found: C, 68.88; H, 10.44; N, 10.15. Mass Spec. (EI, m/z): 263 [M]$^+$.

Example 3

$Li[^tBuC(N^iPr)_2]$. A solution of 1,3-diisopropylcarbodiimide (5.00 g, 39.6 mmol) in $Et_2O$ (50 mL) was cooled to 0° C. $^tBuLi$(23.30 mL of a 1.7 M solution in pentane, 39.6 mmol) was added dropwise via syringe and the mixture was allowed to warm to room temperature. After 30 min the solvent was removed under vacuum affording a yellow oily solid which was dried under vacuum (18 h, 23° C.) to give a pale yellow solid. Trituration with hexane gave $Li[^tBuC(N^iPr)_2]$ as an off-white powder (4.56 g, 61%). $^1H$ NMR (THF-$d_8$): δ 3.84 (sept, $^3J_{HH}$=5.7 Hz, 2H, $CHMe_2$), 1.13 (s, 9H, $CMe_3$), 0.96 (d, $^3J_{HH}$=6.1 Hz, 12H, $CHMe_2$). $^{13}C$ NMR (THF-$d_8$): δ 168.5 (s, $CCMe_3$), 46.6 (d, $^1J_{CH}$=122.3 Hz, $CHMe_2$), 39.4 (s, $CMe_3$), 31.0 (q,$^1J_{CH}$=116.1 Hz, $CHMe_2$), 26.3 (q,$^1J_{CH}$=116.1 Hz, $CMe_3$).

Example 4

Li[$^t$BuC(NCy)$_2$]. A solution of 1,3-dicyclohexylcarbodiimide (5.00 g, 24.2 mmol) in Et$_2$O (50 mL) was cooled to 0° C. $^t$BuLi (14.3 mL of a 1.7 M solution in pentane, 24.2 mmol) was added via syringe and the mixture was allowed to warm to room temperature. After 30 min the volatile components were removed under vacuum affording a yellow oily solid which was dried overnight under vacuum to yield a pale yellow powder. Trituration of this solid with pentane gave Li[$^t$BuC(NCy)$_2$] as a pale yellow powder (4.91 g, 75%). $^1$H NMR (THF-d$_8$): δ 3.50 (m,2H,Cy), 1.81-0.93 (m,20H,Cy), 1.10 (s,9H,CMe$_3$). $^{13}$C NMR (THF-d$_8$): δ 168.3 (s,CCMe$_3$), 55.9 (d,$^1J_{CH}$=119.8 Hz, Cy—C$_1$), 39.5 (s,CMe$_3$), 37.7 (t,$^1J_{CH}$=118.9 Hz,Cy), 31.1 (q,$^1J_{CH}$=117.7 Hz,CMe$_3$), 28.2 (t, partially obscured, Cy), 26.8 (t,$^1J_{CH}$=119.4 Hz, Cy).

Example 5

{$^t$BuC(N$^i$Pr)$_2$}AlCl$_2$. A solution of AlCl$_3$ (1.40 g, 10.5 mmol) in Et$_2$O (30 mL) was cooled to −78° C. and added dropwise to a slurry of Li[$^t$BuC(N$^i$Pr)$_2$] (2.00 g, 10.5 mmol) in Et$_2$O (50 mL) which was also at −78° C. The mixture was warmed to room temperature and stirred for 16 h, affording a slurry of a white solid in a yellow solution. The volatiles were removed under vacuum and the product was extracted from the LiCl with pentane. Concentration of the pentane extract and cooling to 0° C. afforded pure {$^t$BuC(N$^i$Pr)$_2$}AlCl$_2$ as opaque white crystals which were collected by filtration (2.01 g, 68%). $^1$H NMR (CD$_2$Cl$_2$): δ 4.12 (br sept, $^3J_{HH}$=5.9 Hz, H, CHMe$_2$), 1.43 (s,9H,CMe$_3$), 1.18 (d,$^3J_{HH}$=6.2 Hz, 12H, HMe$_2$). $^{13}$C NMR (CD$_2$Cl$_2$): δ 184.3 (s, CCMe$_3$), 46.6 (d,$^1J_{CH}$=135.7 Hz, CHMe$_2$), 40.1 (s,CMe$_3$), 29.2 (q,$^1J_{CH}$=125.7 Hz, CMe$_3$), 25.9 (q,$^1J_{CH}$=124.1 Hz, CHMe$_2$). Anal. Calcd for C$_{11}$H$_{23}$N$_2$AlCl$_2$: C, 46.98; H, 8.24; N, 9.96. Found: C, 46.84; H, 8.12; N, 9.85. Mass Spec. (EI,m/z,$^{35}$Cl): 265 [M]$^+$.

Example 6

{$^t$BuC(NCy)$_2$}AlCl$_2$. A solution of AlCl$_3$ (0.99 g, 7.4 mmol) in Et$_2$O (25 mL) was added dropwise to a slurry of Li[$^t$BuC(NCy)$_2$](2.00 g, 7.4 mmol) in Et$_2$O (50 mL) at −78° C. The mixture was warmed to room temperature and stirred for 18 h, affording a slurry of a white precipitate in a yellow solution. The volatiles were removed under vacuum and the product was extracted from the LiCl with toluene. Concentration of the toluene extract and cooling to 0° C. afforded pure {$^t$Bu(NCy)$_2$}AlCl$_2$ as colorless crystals which were collected by filtration (1.84 g, 69%). $^1$H NMR (CD$_2$Cl$_2$): δ 3.62 (br m,2H,Cy), 1.41 (s,9H,CMe$_3$), 1.91-1.71 (m,4H,Cy), 1.62 (m,2H,Cy), 1.30-1.09 (m,8H+2H,Cy). $^{13}$C NMR (CD$_2$Cl$_2$): δ 184.4 (s,CCMe$_3$), 54.6 (d,$^1J_{CH}$=138.7 Hz, Cy—C$_1$), 40.1 (s, CMe$_3$), 36.9 (t, $^1J_{CH}$=127.9 Hz,Cy), 29.3 (q,$^1J_{CH}$=127.7 Hz, CMe$_3$), 25.7 (t,$^1J_{CH}$=125.7 Hz,Cy), 25.6 (t,$^1J_{CH}$=125.7 Hz,Cy). Anal. Calcd for C$_{17}$H$_{31}$N$_2$AlCl$_2$: C, 56.51; H, 8.65; N, 7.75. Found: C, 56.22; H, 8.70; N, 7.67. Mass Spec. (EI,m/z, $^{35}$Cl) :360[M]$^+$.

Example 7

{$^t$uC(N$^i$Pr)$_2$}AlMe$_2$. A solution of AlMe$_2$Cl (0.25 mL, 2.7 mmol) in Et$_2$O (25 mL) was added dropwise to a slurry of Li[$^t$BuC(N$^i$Pr)$_2$] (0.50 g, 2.6 mmol) in Et$_2$O (30 mL) at −78° C. The reaction mixture was allowed to warm slowly to room temperature and was stirred for 18 h. The volatiles were removed under vacuum and the residue was extracted with pentane. The extract was evaporated to dryness under vacuum yielding {$^t$BuC(N$^i$Pr)$_2$}AlMe$_2$ as a pale yellow solid (0.57 g, 87%). $^1$H NMR (CD$_2$Cl$_2$): δ 4.07 (sept,$^3J_{HH}$= 6.2 Hz,2H,CHMe$_2$), 1.38 (s,9H,CMe$_3$), 1.06 (d,$^3J_{HH}$=6.1 Hz,12H,CHMe$_2$), −0.81 (s,6H,AlMe$_2$). $^{13}$C NMR (CD$_2$Cl$_2$): δ 178.4 (s,CCMe$_3$), 45.8 (d,$^1J_{CH}$=135.3 Hz,CHMe$_2$), 40.0 (s,CMe$_3$), 29.7 (q,$^1J_{CH}$=127.0 Hz, CHMe$_2$), 26.3 (q,$^1J_{CH}$=125.5 Hz,CMe$_3$), −9.06 (br q,$^1J_{CH}$=117.7 Hz,AlMe$_2$). Anal. Calcd for C$_{13}$H$_{29}$N$_2$Al: C, 64.96; H, 12.16; N, 11.65. Found: C, 64.46; H, 11.90; N, 11.90. Mass Spec. (EI,m/z): 240 [M]$^+$, 225 [M—CH$_3$]$^+$.

Example 8

{$^t$BuC(NCy)$_2$}AlMe$_2$. A solution of AlMe$_2$Cl (0.71 mL, 7.7 mmol) in Et$_2$O (30 mL) was added dropwise to a slurry of Li[$^t$BuC(NCy)$_2$] (2.00 g, 7.4 mmol) in Et$_2$O (40 mL) at −78° C. The mixture was allowed to warm to room temperature and was stirred for 15 h. The volatiles were removed under vacuum and the residue was extracted with pentane (3×15 mL). The extract was concentrated to 30 mL and maintained at room temperature affording {$^t$BuC(NCy)$_2$}AlMe$_2$(2.00 g, 83%) as large colorless crystals which were collected by filtration. $^1$H NMR (CD$_2$Cl$_2$): δ 3.56 (m,2H,Cy), 1.80-1.69 (m,8H,Cy), 1.61-1.57 (m,2H, Cy), 1.36 (s,9H,CMe$_3$), 1.27-1.03 (m,8H+2H,Cy), −0.83 (s,6H,AlMe$_2$). $^{13}$C NMR (CD$_2$Cl$_2$): δ 178.5 (s,CCMe$_3$), 54.2 (d,$^1J_{CH}$=125.9 Hz, Cy—C$_1$), 39.9 (s,CMe$_3$), 37.3 (t,$^1J_{CH}$=119.3 Hz,Cy), 29.7 (q,$^1J_{CH}$=117.3 Hz,CMe$_3$), 26.1 (t,$^1J_{CH}$=119.3 Hz,Cy), 26.0 (t,$^1J_{CH}$=119.3 Hz, Cy), −9.1 (br q,$^1J_{CH}$=103.9 Hz,AlMe$_2$). Anal. Calcd for C$_{19}$H$_{37}$N$_2$Al: C, 71.20; H, 11.64; N, 8.74. Found: C, 71.18; H, 11.88; N, 8.73. mass Spec. (EI,m/z): 320 [M]$^+$, 305 [M—CH$_3$]$^+$.

Example 9

{$^t$BuC(N$^i$Pr)$_2$}Al(CH$_2$Ph)$_2$. A solution of {$^t$BuC(N$^i$Pr)$_2$}AlCl$_2$ (0.50 g, 1.8 mmol) in Et$_2$O (25 mL) was cooled to −78° C. and PhCH$_2$MgCl (3.56 mL of a 1.0 M solution in Et$_2$O, 3.6 mmol) was added dropwise via syringe. The reaction mixture was allowed to warm to room temperature and was stirred for 15 h. The volatiles were removed under vacuum and the residue was extracted with pentane. The extract was evaporated to dryness under vacuum affording pure {$^t$BuC(N$^i$Pr)$_2$}Al(CH$_2$Ph)$_2$ as a viscous oil (0.55 g, 79%) that was induced to solidify through storage at −40° C. $^1$H NMR (CD$_2$Cl$_2$): δ 7.11 (t,$^3J_{HH}$=7.6 Hz,4H,m-Ph), 7.02 (d,$^3J_{HH}$=6.9 Hz,4H,o-Ph), 6.88 (t,$^3J_{HH}$= 7.3 Hz,2H,p-Ph), 4.00 (sept,$^3J_{HH}$=6.2 Hz,2H,CHMe$_2$), 1.75 (s,4H,CH$_2$Ph), 1.34 (s,9H,CMe$_3$), 0.94 (d,$^3J_{HH}$=6.2 Hz, 12H, CHMe$_2$). $^{13}$C NMR (CD$_2$Cl$_2$): δ 180.8 (s,CCMe$_3$), 146.8 (s,ipso-Ph), 128.2 (d,$^1J_{CH}$=155.8 Hz, o- or m-Ph), 127.5 (d,$^1J_{CH}$=149.4 Hz, o- or m-Ph), 121.7 (d,$^1J_{CH}$=148.5 Hz,p-Ph), 45.6 (d,$^1J_{CH}$=128.9 Hz,CHMe$_2$), 40.1 (s,CMe$_3$), 29.6 (q,$^1J_{CH}$=119.0 Hz,CMe$_3$), 26.3 (q,$^1J_{CH}$=116.4 Hz,CHMe$_2$), 21.4 (br t,$^1J_{CH}$=108.9 Hz, CH$_2$Ph). Anal. Calcd for C$_{25}$H$_{37}$N$_2$Al: C, 76.49; H, 9.50; N, 7.14. Found: C, 75.05; H, 9.63; N, 6.89. Mass Spec. (EI,mlz): 301 [M—CH$_2$Ph]$^+$.

Example 10

{$^t$Buc(NCy)$_2$}Al(CH$_2$Ph)$_2$. A solution of {$^t$BuC(NCy)$_2$}AlCl$_2$(0.50 g, 1.4 mmol) in Et$_2$O (20 mL) was cooled to −78° C. and PhCH$_2$MgCl (2.76 mL of a 1.0 M solution in Et$_2$O, 2.8 mmol) was added dropwise by syringe. The mixture was allowed to warm slowly to room temperature and was stirred for 15 h. The volatiles were removed under vacuum and the residue was extracted with pentane. The extract was evaporated under vacuum affording pure {$^t$BuC(NCy)$_2$}Al(CH$_2$Ph)$_2$ as a viscous white oil. (0.57 g, 87%).

$^1$H NMR (CD$_2$Cl$_2$): δ 7.08 (t,$^3$J$_{HH}$=7.6 Hz,4H,m-Ph), 6.98 (d,$^3$J$_{HH}$=6.9 Hz,4H, o-Ph) , 6.84 (t,$^3$J$_{HH}$=7.3 Hz,2H,p-Ph), 3.44 (m,2H,Cy), 1.69 (s,4H,CH$_2$Ph), 1.63-1.51 (m,4H+2H, Cy), 1.27 (s,9H,CMe$_3$), 1,21-0.78 (m,14H,Cy). $^{13}$C NMR (CD$_2$Cl$_2$): δ 180.8 (s,CCMe$_3$), 146.9 (s,ipso-Ph), 126.2 (d,$^1$J$_{CH}$=155.8 Hz, o- or m-Ph), 127.5 (d,$^1$J$_{CH}$=147.6 Hz, o- or m-Ph), 121.6 (d,J$_{CH}$=151.3 Hz,p-Ph), 54.0 (d, partially obscured, Cy—C$_1$), 40.0 (s,CMe$_3$), 37.1 (t,$^1$J$_{CH}$=117.7 Hz,Cy), 29.6 (q,$^1$J$_{CH}$=117.3 Hz,CMe$_3$), 25.9 (t,$^1$J$_{CH}$=18.2 Hz,Cy), 25.7 (t,$^1$J$_{CH}$=118.2 Hz,Cy), 21.4 (t,$^1$J$_{CH}$=108.7 Hz,CH$_2$Ph). Anal. Calcd for C$_{31}$H$_{45}$N$_2$Al: C, 78.77; H, 9.60; N, 5.93. Found: C, 78.62; H, 9.58; N, 5.83.

Example 11

{$^t$BuC(N$^i$Pr)$_2$}Al(CH$_2$CMe$_3$)$_2$. {$^t$BuC(N$^i$Pr)$_2$}AlCl$_2$ (0.50 g, 1.8 mmol) and LiCH$_2$CMe$_3$ (0.28 g, 3.6 mmol) were mixed as solids in the glove box. Et$_2$O (40 mL) was added at −78° C. and the mixture was allowed to warm slowly to room temperature, affording a colorless solution and a white precipitate. The mixture was stirred for 18 h and the volatiles were removed under vacuum. The residue was extracted with pentane (3×10 mL). The extract was taken to dryness under vacuum affording {$^t$BuC(N$^i$Pr)$_2$}Al(CH$_2$CMe$_3$)$_2$ as a white solid (0.58 g, 93%). $^1$H NMR (CD$_2$Cl$_2$): δ 4.13 (sept,$^3$J$_{HH}$=6.2 Hz, CHMe$_2$), 1.39 (s,9H,CMe$_3$), 1.15 (d,$^3$J$_{HH}$=6.3 Hz, CHMe$_2$), 0.99 (s,18H,CH$_2$CMe$_3$), 0.27 (s,4H,CH$_2$CMe$_3$). $^{13}$C NMR (CD$_2$Cl$_2$): δ 179.7 (s,CCMe$_3$), 46.1 (d,$^1$J$_{CH}$=121.0 Hz,CHMe$_2$), 40.1 (s,CMe$_3$), 35.2 (q, J$_{CH}$=112.2 Hz, CH$_2$CMe$_3$), 32.1 (br t, partially obscured, CH$_2$CMe$_3$), 31.6 (s, CH$_2$CMe$_3$), 29.8 (q,$^1$J$_{CH}$=121.2 Hz,CMe$_3$), 26.6 (q,$^1$J$_{CH}$=117.9 Hz, CHMe$_2$). Anal. Calcd for C$_{21}$H$_{45}$N$_2$Al: C, 71.54; H, 12.86; N, 7.95. Found: C, 70.46; H, 12.82; N, 7.72. Mass Spec. (EI,m/z): 281 [M—CH$_2$CMe$_3$]$^+$.

Example 12

{$^t$BuC(NCy)$_2$}Al(CH$_2$CMe$_3$)$_2$. A solution of LiCH$_2$CMe$_3$ (0.43 g, 5.5 mmol) in Et$_2$O (20 mL) was added dropwise at −78° C. to an Et$_2$O solution (30 mL) of {$^t$BuC(NCy)$_2$}AlCl$_2$ (1.00 g, 2.8 mmol). The reaction mixture was allowed to warm slowly to room temperature and was stirred for 15 h. The volatiles were removed under vacuum and the residue was extracted with pentane. The extract was evaporated to dryness under vacuum to afford pure {$^t$BuC(NCy)$_2$}Al(CH$_2$CMe$_3$)$_2$ as a white solid material (1.13 g, 94%). $^1$H NMR (CD$_2$Cl$_2$): δ 3.63 (m,2H,Cy), 1.86-1.71 (m,8H,Cy), 1.60 (m,2H,Cy), 1.36 (s,9H,CMe$_3$), 1.30-1.09 (m,8H+2H, Cy), 0.99 (s,CH$_2$CMe$_3$), 0.25 (s,4H,CH$_2$CMe$_3$). $^{13}$C NMR (CD$_2$Cl$_2$): δ 179.7 (s,CCMe$_3$), 54.8 (d,$^1$J$_{CH}$=126.8 Hz, Cy—C$_1$), 40.0 (s,CMe$_3$), 37.2 (t,$^1$J$_{CH}$=124.3 Hz,Cy), 35.2 (q,$^1$J$_{CH}$=117.6 Hz, CH$_2$CMe$_3$), 32.1 (br t, partially obscured, CH$_2$CMe$_3$), 31.6 (s,CH$_2$CMe$_3$), 29.8 (q,$^1$J$_{CH}$=119.6 Hz, CMe$_3$), 26.2 (t,$^1$J$_{CH}$=118.2 Hz, Cy), 26.1 (t,$^1$J$_{CH}$=118.2 Hz, Cy). Anal. Calcd for C$_{27}$H$_{53}$N$_2$Al: C, 74.95; H, 12.35; N, 6.47. Found: C, 73.87; H, 12.42; N, 6.60. Mass Spec. (EI,m/z): 362 [M—CH$_2$CMe$_3$]$^+$.

Example 13

[({MeC(N$^i$Pr)$_2$}AlMe)$_2$(μ-Me)][MeB(C$_6$F$_5$)$_3$]. A solution of B(C$_6$F$_5$)$_3$ (0.77 g, 1.5 mmol) in CH$_2$Cl$_2$ (20 mL) was added to {MeC(N$^i$Pr)$_2$}AlMe$_2$ (0.60 g, 3.0 mmol) also in CH$_2$Cl$_2$(15 mL). The reaction mixture was allowed to stir for 30 min at room temperature and the volatiles were removed under vacuum leaving an oily white solid. Trituration with pentane afforded [({MeC(N$^i$Pr)$_2$}AlMe)$_2$(μ-Me)][MeB(C$_6$F$_5$)$_3$] as a white powder (0.91 g, 83%). $^1$H NMR (CD$_2$Cl$_2$,293 K): δ 3.79 (sept,$^3$J$_{HH}$=6.6 Hz,4H, CHMe$_2$), 2.31 (s,6H,CMe), 1.28 (d,$^3$J$_{HH}$=6.5 Hz,24H, CHMe$_2$), −0.38 (br s,9H,AlMe). $^1$H NM (CD$_2$Cl$_2$, 193K): δ 3.79 (br sept,2H,CHMe$_2$), 3.67 (br sept,6H,CHMe$_2$), 2.33 (s,6H,CMe), 2.15 (s,6H,CMe), 1.30 (m,18H,CHMe$_2$), 1.18 (m,12H,CHMe$_2$), 1.02 (m,18H,CHMe$_2$), −0.17 (s, 6H, AlMe), −0.54 (s, 6H, AlMe), −0.75 (s, 6H, AlMe). $^{11}$B NMR (CD$_2$Cl$_2$): δ −13.4 (br s, MeB(C$_6$F$_5$)$_3$). $^{13}$C NMR (CD$_2$Cl$_2$): δ 182.0 (s,CMe), 50.5 (d,$^1$J$_{CH}$=138.9 Hz, CHMe$_2$), 23.4 (q,$^1$J$_{CH}$=127.0 Hz, CHMe$_2$), 17.8 (q,$^1$J$_{CH}$=130.3 Hz, CMe), −5.6 (br q,$^1$J$_{CH}$=130.3 Hz, AlMe). Anal. Calcd for C$_{38}$H$_{46}$N$_4$Al$_2$BF$_{15}$: C, 50.23; H, 5.10; N, 6.17. Found: C, 50.46; H, 4.92; N, 6.09.

Example 14

([{MeC(N$^i$Pr)$_2$}AlMe(NMe$_2$Ph)][B(C$_6$F$_5$)4]). A CD$_2$Cl$_2$ solution (600 μL) of [HNMe$_2$Ph][B(C$_6$F$_5$)$_4$] (85.3 mg, 0.11 mmol) was added to a vial containing {MeC(N$^i$Pr)$_2$}AlMe$_2$ (21.1 mg, 0.11 mmol). The mixture was transferred to an NMR tube and NMR spectra were recorded showing complete conversion to [{MeC(N$^i$Pr)$_2$}AlMe(NMe$_2$Ph)][B(C$_6$F$_5$)$_4$]. $^1$H NMR (CD$_2$Cl$_2$: δ 7.63 (t,$^3$J$_{HH}$=7.9 Hz,2H,m-Ph), 7.51 (t,$^3$J$_{HH}$=7.3 Hz,1H,p-Ph), 7.47 (d,$^3$J$_{HH}$=7.9 Hz,2H, o-Ph), 3.58 (sept,$^3$J$_{HH}$=6.4 Hz, 2H,CHMe$_2$), 3.20 (s, 6H, NMe$_2$Ph), 2.17 (s, 3H, CMe), 1.03 (d,$^3$J$_{HH}$=6.5 Hz, 6H, CHMe$_2$), 0.92 (d,$^3$J$_{HH}$=6.4 Hz, 6H, CHMe$_2$), −0.30 (s, 3H, AlMe). $^{13}$C NM (CD$_2$Cl$_2$): δ 182.0 (s,CMe), 143.7 (s, ipso-Ph) , 131.4 (d,$^1$J$_{CH}$=159.4 Hz, o-Ph), 129.8 (d,$^1$J$_{CH}$= 164.8 Hz, p-Ph), 120.9 (d,$^1$J$_{CH}$=153.1 Hz, m-Ph), 46.7 (q,$^1$J$_{CH}$=134.7 Hz, NMe$_2$), 46.0 (d,$^1$J$_{CH}$=125.2 Hz, CHMe$_2$), 24.7 (q,$^1$J$_{CH}$=119.7 Hz, CHMe$_2$), 24.6 (q,$^1$J$_{CH}$=119.7 Hz, CHMe$_2$), 12.7 (q,$^1$J$_{CH}$=122.6 Hz, CMe), −13.4 (br q,$^1$J$_{CH}$= 116.8 Hz, AlMe).

Example 15

([{MeC(N$^i$Pr)$_2$}AlMe(PMe$_3$)][MeB(C$_6$F$_5$)$_3$]. A CD$_2$Cl$_2$ solution of [({MeC(N$^i$Pr)$_2$}AlMe)$_2$(μ-Me)][MeB(C$_6$F$_5$)$_3$] was cooled in liquid N$_2$ and PMe$_3$ (5 equiv) was condensed onto the frozen solution. The mixture was warmed to room temperature and the $^1$H NMR spectrum was recorded, showing that complete formation of the trimethylphosphine adduct [{MeC(N$^i$Pr)$_2$}AlMe(PMe$_3$)] [MeB(C$_6$F$_5$)$_3$] and {MeC(N$_i$Pr)$_2$}AlMe$_2$ had occurred. To obtain a sample free from reaction byproducts, the NMR tube was evacuated and pumped on for 18 h. The resulting oily solid was redissolved in CD$_2$Cl$_2$ and the NMR spectra was recorded, and showed that only [{MeC(N$^i$Pr)$_2$}AlMe(PMe$_3$)][MeB(C$_6$F$_5$)$_3$] was present. $^1$H NMR (CD$_2$Cl$_2$): δ 3.62 (sept,$^3$J$_{HH}$=6.3 Hz, 2H, CHMe$_2$), 2.17 (s, 3H, CMe), 1.52 (d,$^2$J$_{PC}$=9.4 Hz, 9H, PMe$_3$), 1.10 (d,$^3$J$_{HH}$=6.3 Hz, 12H, CHMe$_2$), −0.27 (s, 3H, AlMe). $^{31}$P NMR (CD$_2$Cl$_2$): δ −34.55 (s,PMe$_3$). $^{13}$C NMR (CD$_2$Cl$_2$): δ 180.6 (s, CMe), 45.5 (d,$^1$J$_{CH}$=131.1 Hz, CHMe$_2$), 25.3 (q,$^1$J$_{CH}$=121.0 Hz, CHMe$_2$), 12.4 (q,$^1$J$_{CH}$= 124.7 Hz, CMe), 9.1 (dq,$^1$J$_{PC}$=29.6 Hz,$^1$J$_{CH}$=127.6 Hz, PMe$_3$), −12.8 (br q,$^1$J$_{CH}$=10$^{9.6}$ Hz, AlMe).

Example 16

[{MeC(N$^i$Pr)$_2$}AlMe(PMe$_3$)][B(C$_6$F$_5$)$_4$]. A CD$_2$Cl$_2$ solution of [{MeC(N$^i$Pr)$_2$}AlMe(NMe$_2$Ph)][B(C$_6$F$_5$)$_4$] was cooled in liquid N$_2$ and PMe$_3$ (5 equiv) was condensed onto the frozen solution. The mixture was warmed to room temperature and the $^1$H NMR spectrum was recorded, showing that formation of the trimethylphosphine adduct [{MeC(N$^i$Pr)$_2$}AlMe(PMe$_3$)][B(C$_6$F$_5$)$_4$] and free NMe$_2$Ph had occurred. $^1$H NMR (CD$_2$Cl$_2$): δ 3.62 (sept, $^3$J$_{HH}$=6.3 Hz, 2H, CHMe$_2$), 2.17 (s, 3H, CMe), 1.52 (d, $^2$J$_{PC}$=9.4 Hz, 9H, PMe$_3$), 1.10 (d, $^3J_{HH}$=6.3 Hz, 12H, CHMe$_2$), −0.27 (s, 3H, AlMe). $^{31P}$NMR (CD$_2$Cl$_2$: δ −34.55 (s, PMe$_3$). $^{13}$C NMR (CD$_2$Cl$_2$): δ 180.6 (s, CMe), 45.5 (d, $^1J_{CH}$=131.1 Hz, CHMe$_2$), 25.3 (q, $^1J_{CH}$=121.0 Hz, CHMe$_2$), 12.4 (q, $^1J_{CH}$=124.7 Hz, CMe) , 9.1 (dq, $^1J_{PC}$=29.6 Hz, $^1J_{CH}$=127.6 Hz, PMe$_3$), −12.8 (br q, $^1J_{CH}$=109.6 Hz, AlMe).

Based upon the above synthesis illustration Examples 1-16, it can be seen that the cationic aluminum alkyl complexes are prepared by reacting a neutral precursor complex of the type R$^2$C(NR$^1$) (NR$^3$)AlX$_2$, where R$^1$, R$^2$, R$^3$ and X are as defined above, with an activator compound which is capable of abstracting one X— group from the precursor complex or of cleaving one Al—X bond of the precursor complex. Additionally, example 15 shows that the {MeC(N$^i$Pr)$_2$}AlMe$_2$ moiety of [{MeC(N$^i$Pr)$_2$}AlMe)$_2$(μ-Me][MeB(C$_6$F$_5$)$_3$] can be displaced by the Lewis base PMe$_3$, and example 16 shows that the NMe$_2$Ph group of [{MeC(N$^i$Pr)$_2$}AlMe(NMe$_2$Ph)][B(C$_6$F$_5$)$_4$] can be displaced by PMe$_3$.

The following two additional examples illustrate the preparation of base-free cations.

Example 17

[{$^t$BuC(N$^i$Pr)$_2$}AlMe][MeB(C$_6$F$_5$)3]. A solution of {$^t$BuC(N$^i$Pr)$_2$}AlMe$_2$ (0.041 g, 0.17 mmol) in toluene (1.5 cm$^3$) was prepared in the dry box. This was added dropwise via pipette to a solution of 1 equiv B(C$_6$F$_5$)$_3$ (0.087 g, 0.17 mmol) also in toluene (2.5 cm$^3$) that was rapidly stirring in an ampoule fitted with a teflon tap. The ampoule was sealed and the mixture was removed from the dry box and stirred on a vacuum line for 30 mins. The volatiles were then removed under reduced pressure, leaving an off-white, oily residue. (CD$_2$Cl)$_2$ was added to this residue and the solution transferred to an NMR tube. The $^1$H NMR spectrum was recorded immediately and showed complete conversion to the desired base-free cation [{$^t$BuC(N$^i$Pr)$_2$}AlMe][MeB (C$_6$F$_5$)$_3$]. $^1$H NMR (CD$_2$Cl$_2$): δ 4.12 (sept,$^3J_{HH}$=6.2 Hz, 2H, CHMe$_2$), 1.67 (br s, 3H, BCH$_3$), 1.42 (s, 9H, CMe$_3$), 1.09 (d, $^6$H,$^3J_{HH}$=6.2 Hz, CHMe$_2$), 0.96 (d, 6H,$^3J_{HH}$=6.2 Hz, CHMe$_2$), −0.44 (br s, 3H, AlMe) . $^{13}$C NMR (CD$_2$Cl)$_2$: δ 181.3 (s, CCMe$_3$), 46.0 (d,$^1J_{CH}$=132.1 Hz, CHMe$_2$), 40.1 (s, CMe$_3$), 29.3 (q,$^1J_{CH}$=122.3 Hz, CMe$_3$), 26.4 (q,$^1J_{CH}$=125.3 Hz, CHMe$_2$), 25.5 (q,$^1J_{CH}$=121.2 Hz, CHMe$_2$),16.8 (br q, $^1J_{CH}$=108.0 Hz, Me-B), −8.7 (br q,$^1J_{CH}$=118.1 Hz, AlMe). C$_6$F$_5$ resonances were also observed.

Example 18

([{$^t$BuC(NCy)$_2$}AlMe][MeB(C$_6$F$_5$)$_3$]). The product was prepared in an identical manner to that outlined above, using 0.033 g {$^t$BuC(NCy)$_2$}AlMe$_2$ (0.10 mmol) and 0.053 g B(C$_6$F$_5$)$_3$ (1 equiv, 0.10 mmol). Again 100% conversion to the base-free cation was observed. $^1$H NMR (CD$_2$Cl)$_2$: δ 3.61 (m, 2H, Cy), 1.83-1.74 (br m, 4H, Cy), 1.66 (br s, 3H, BCH$_3$), 1.55 (br t, 4H, Cy), 1.37 (s, 9H, CMe$_3$), 1.25-0.98 (m, 8H, Cy), 0.89-0.79 (m, 4H, Cy), −0.46 (s, 3H, AlMe). $^{13}$C NMR (CD$_2$Cl)$_2$: δ 181.1 (s, CCMe$_3$), 54.1 (d,$^1J_{CH}$=134.0 Hz, Cy—C$_1$), 39.9 (s, CMe$_3$), 37.5 (t,$^1J_{CH}$=129.0 Hz, Cy), 36.6 (t,$^1J_{CH}$=126.2 Hz, Cy), 29.3 (q,$^1J_{CH}$=122.3 Hz, CMe$_3$), 25.8 (t,$^1J_{CH}$=122.5 Hz, Cy), 16.8 (br q, B-Me), −8.5 (q,$^1J_{CH}$=114.7 Hz, AlMe). C$_6$F$_5$ resonances were also observed.

Example 19

Polymerization Procedure for Ethylene

All polymerizations were carried out using transition metal-free conditions, employing glass apparatus and Teflon-coated stirrer bars.

In a typical experiment, 0.02 g of {$^t$BuC(N$^i$Pr)$_2$}AlMe$_2$ was weighed out into a glass vial in the dry box, and 3 mL of dry toluene was added. 1 equiv of activator, based on the aluminum compound was weighed into a Fisher-Porter bottle and ca. 50 cm$^3$ of toluene was added. The aluminum complex solution was added dropwise over 2 minutes (using a pipette) to the rapidly stirring activator solution, ensuring efficient mixing of the 2 components, and a constant excess of activator (to limit formation of base adduct species). The apparatus was then removed from the dry box and connected to the polymerization equipment, consisting of an ethylene cylinder, vacuum line and gas purification system. This had been previously evacuated to remove any residual gas from the system. The mixture was allowed to equilibrate at the temperature required for the experiment (10–20 minutes) before the introduction of ethylene. The Fisher-Porter bottle was placed under slight vacuum prior to introduction of the ethylene, to reduce the nitrogen content within and maximize ethylene dissolution in the solvent). The polymerization was typically allowed to run for 60 minutes, after which time the ethylene flow to the system was halted. The apparatus was vented in a fume hood and disassembled. 50–80 mL of a mixture of methanol (ca. 150 mL) and conc. HCl (ca. 1.5 mL) was added to the solution to quench the reaction and the precipitate (if any) was collected by filtration. The polymer was then washed with acidified water (ca. 1.5 mL conc. HCl in 100 mL H$_2$O) to ensure removal of the Al-salts, and dried in a vacuum oven at 60° C. for 2–8 hours. The weight was recorded and the activity calculated (see table).

The results of the ethylene polymerizations are summarized in the table below.

Table of Results for Ethylene Polymerization
(neutral precursor complex = {$^t$BuC(N$^i$iPr)$_2$}AlMe$_2$; ethylene pressure = 2 atm; solvent = toluene)

| Run | Activator Compound | Time (mins) | Temp (° C.) | Yield PE (g) | Activity* |
|---|---|---|---|---|---|
| 1 | B(C$_6$F$_5$)$_3$ | 60 | 26 | 0.053 | 293 |
| 2 | B(C$_6$F$_5$)$_3$ | 60 | 60 | 0.115 | 697 |
| 3 | B(C$_6$F$_5$)$_3$ | 60 | 85 | 0.026 | 162 |
| 4 | [Ph$_3$C][B(C$_6$F$_5$)$_4$] | 60 | 26 | 0.084 | 530 |
| 5 | [Ph$_3$C][B(C$_6$F$_5$)$_4$] | 60 | 60 | 0.293 | 1777 |
| 6 | [Ph$_3$C][B(C$_6$F$_5$)$_4$] | 30** | 60 | 0.266 | 3183 |
| 7 | [Ph$_3$C][B(C$_6$F$_5$)$_4$] | 30** | 85 | 0.351 | 4145 |

*g PE/mol cat*hr*atm
**= solution stopped stirring due to formation of a precipitate therefore stopped after 30 mins

Examples 20–26

Additional Aluminum Amidinate Complexes

Example 20

{$^t$BuC(N$^i$Pr)$_2$}Al$^i$Bu$_2$. A solution of Al$^i$Bu$_2$Cl (2.50 mL, 13.1 mmol) in Et$_2$O (40 mL) was added dropwise to a slurry of Li[$^t$BuC(N$^i$Pr)$_2$] (2.50 g, 13.1 mmol) in Et$_2$O (75 mL) at −50° C. The reaction mixture was allowed to warm to room temperature and was stirred for 16 h, resulting in a slurry of a white solid in a yellow solution. The volatiles were removed under vacuum, the crude product was extracted with pentane and the volatiles were removed from the extract under vacuum to afford {$^t$BuC(N$^i$Pr)$_2$}Al$^i$Bu$_2$ as a yellow liquid. Yield 3.55 g, 83%. $^1$H NMR (CD$_2$Cl$_2$): δ 4.09 (sept, $^3J_{HH}$= 6.2, 2H, NCHMe$_2$), 1.84 (m, $^3J_{HH}$=6.8, 2H, CH2CHMe$_2$), 1.38 (s, 9H, CMe$_3$), 1.10 (d, $^3J_{HH}$=6.5, 12H, CHMe$_2$), 0.92 (d, $^3J_{HH}$=6.8, 12H, CHMe$_2$), -0.01 (d, $^3J_{HH}$= 6.8, 4H, AlCH$_2$). $^{13}$C NMR (CD$_2$Cl$_2$): δ 178.6 (s, CCMe$_3$), 45.6 (d, $^1J_{CH}$=135, NCHMe$_2$), 40.0 (s, CMe$_3$), 29.7 (q, $^1J_{CH}$=125, CMe$_3$), 28.6 (q, $^1J_{CH}$=123, $^i$Pr or $^i$Bu—CHMe$_2$), 27.0 (d, $^1J_{CH}$=120, CH$_2$CHMe$_2$), 26.3 (q, $^1J_{CH}$=125, $^i$Pr or $^i$Bu—CHMe$_2$), 23.4 (br t, $^1J_{CH}$=107, AlCH$_2$).

Example 21

{MeC(NAd)$_2$}AlMe$_2$. A solution of AlMe$_3$ (0.132 g, 1.84 mmol) in hexane (10 mL) was added dropwise to a rapidly stirred solution of 1,3-diadamantylcarbodimide (0.500 g, 1.61 mmol) in hexane (30 mL). The reaction mixture was stirred at room temperature for 18 h, and the volatiles were removed under vacuum affording pure {MeC(NAd)$_2$}AlMe$_2$ as a white solid (0.62 g, 88%). Analytically pure samples were obtained by recrystallization from Et$_2$O at -30° C. $^1$H NMR (CD$_2$Cl$_2$): δ 2.22 (s, 3H, CMe), 2.03 (br s, 6H, Ad—Hγ), 1.79 (br d, $^2J_{HH}$=2.88, 12H, Ad—Hβ), 1.65 (br s, 12H, Ad—Hδ), -0.82 (s, 6H, AlMe$_2$). $^{13}$C NMR (CD$_2$Cl$_2$): δ 172.6 (s, CMe), 51.5 (s, Ad—Cα), 44.6 (t, $^1J_{CH}$=129, Ad—Cβ), 36.8 (t, $^1J_{CH}$=126, Ad—Cδ), 30.3 (d, $^1J_{CH}$=132, Ad—Cγ), 19.7 (q, $^1J_{CH}$=128, CMe), -9.6 (br q, $^1J_{CH}$=112, AlMe$_2$). Anal. Calcd for C$_{24}$H$_{39}$AlN$_2$: C, 75.35; H, 10.27; N, 7.32. Found: C, 74.96; H, 10.35; N, 7.30.

Example 22

{$^t$BuC(NAd)$_2$}AlMe$_2$. A solution of 1,3-diadamantylcarbodimide (2.64 g, 8.50 mmol) in Et$_2$O (80 mL) was cooled to 0° C. $^t$BuLi (5.0 mL of a 1.7 M solution in hexanes, 8.5 mmol) was added slowly by syringe. The resulting mixture was allowed to warm to room temperature and was stirred for 2 h. The mixture was cooled to -78° C. and a solution of AlMe$_2$Cl (0.79 mL, 8.5 mmol) in Et$_2$O (30 mL) was added. The resulting solution was allowed to warm to room temperature and was stirred for 18 h. The volatiles were removed under vacuum and the product was extracted from the LiCl with pentane. The pentane extract was concentrated and cooled to -30° C. to afford {$^t$BuC(NAd)$_2$}AlMe$_2$ as white crystals which were isolated by filtration (0.47 g, 13% based on AlMe$_2$Cl). The low isolated yield is due to the high solubility of the product. $^1$H NMR (CD$_2$Cl$_2$): δ 2.05 (br s, 6H, Ad—Hγ), 2.02 (s br, 12H, Ad—Hβ), 1.62 (br s, 12H, Ad—Hδ), 1.47 (s, 9H, CMe$_3$), -0.76 (s, 6H, AlMe$_2$). $^{13}$C NMR (CD$_2$Cl$_2$): δ 182.5 (s, CCMe$_3$), 55.0 (s, Ad—Cα), 46.0 (t, $^1J_{CH}$=128, Ad—Cβ), 38.5 (s, CMe$_3$), 36.6 (t, $^1J_{CH}$=126, Ad—Cδ), 32.6 (q, $^1J_{CH}$= 127, CMe$_3$), 30.7 (d, $^1J_{CH}$=133, Ad—Cγ), -6.8 (br q, $^1J_{CH}$=113, AlMe$_2$). Anal. Calcd for C$_{27}$H$_{45}$AlN$_2$: C, 76.37; H, 10.68; N, 6.60. Found: C, 76.43; H, 10.86; N, 6.65. The structure of this compound was confirmed by X-ray crystallography.

Example 23

{MeC(NAr)$_2$}AlMe$_2$ (Ar=2,6-$^i$Pr$_2$C$_6$H$_3$). This compound was prepared by the procedure described for {MeC(NAd)$_2$}AlMe$_2$, using 0.525 g 1,3-bis(2,6-diisopropylphenyl)carbodimide (1.45 mmol) in 40 mL hexane and 0.111 g AlMe$_3$ (1.53 mmol) in 10 mL hexane. After 18 h the volatiles were removed under vacuum yielding pure {MeC(NAr)$_2$}AlMe$_2$ as an off-white solid. (0.491 g, 74%). $^1$H NMR (CD$_2$Cl$_2$): δ 7.19 (m, 6H, NAr) , 3.35 (sept, $^3J_{HH}$=6.8, 41, CHMe$_2$), 1.49 (s, 3H, CMe), 1.23 (d, $^3J_{HH}$= 7.6, 12H, CHMe$_2$), 1.21 (d, $^3J_{HH}$=7.2, 12H, CHMe$_2$), -0.53 (s, 6H, AlMe$_2$). $^{13}$C NMR (CD$_2$Cl$_2$): δ 176.1 (s, CMe), 145.1 (s, Ar—C$_{ortho}$), 138.4 (s, Ar—C$_{ipso}$), 126.3 (d, $^1J_{CH}$= 160, Ar—C$_{para}$), 123.8 (d, $^1J_{CH}$=156, Ar—C$_{meta}$), 28.5 (d, $^1J_{CH}$=126, CHMe$_2$), 24.7 (q, $^1J_{CH}$=126, CHMe$_2$), 23.9 (q, $^1J_{CH}$=126, CHMe$_2$), 14.4 (q, $^1J_{CH}$=129, CMe), -9.9 (q, $^1J_{CH}$=113, AlMe$_2$).

Example 24

{$^t$BuC(NAr)$_2$}AlCl$_2$. This compound was prepared by the procedure described for {$^t$BuC(NAd)$_2$}AlMe$_2$, using 2.85 g 1,3-bis(2,6-diisopropylphenyl)carbodimide (7.86 mmol) in 80 mL Et$_2$O, 4.6 mL $^t$BuLi (1.7 M solution in pentane, 7.9 mmol) and 1.05 g AlCl$_3$ (7.86 mmol) in 30 mL Et$_2$O. After 18 h the volatiles were removed under vacuum yielding an oily yellow solid. {$^t$BuC(NAr)$_2$}AlCl$_2$ was extracted from LiCl with pentane and isolated from the extract by crystallization at -30° C. Yield 0.687 g, 17% based on AlCl$_3$). $^1$H NMR (CD$_2$Cl$_2$): δ 7.27 (d, $^3J_{HH}$=6.5, 1H, Ar), 7.24 (d, $^3J_{HH}$=6.8, 1H, Ar), 7.19 (s, 3H, Ar), 7.17 (d, 1H, Ar), 3.41 (sept, $^3J_{HH}$=6.7, 4H, CHMe$_2$), 1.36 (d, $^3J_{HH}$=6.5, 12H, CHMe$_2$), 1.27 (d, $^3J_{HH}$=6.8, 12H, CHMe$_2$), 0.98 (s, 9H, CMe$_3$). $^{13}$C NMR (CD$_2$Cl$_2$): δ 187.3 (s, CCMe$_3$), 145.3 (s, Ar—C$_{ortho}$), 136.6 (s, Ar—C$_{ipso}$), 127.4 (d, $^1J_{CH}$=159, Ar—C$_{para}$), 124.2 (d, $^1J_{CH}$=157, Ar—C$_{meta}$), 42.5 (s, CMe$_3$), 29.4 (q, $^1J_{CH}$=128, CMe$_3$), 29.1 (d, $^1J_{CH}$=128, CHMe$_2$), 27.3 (q, $^1J_{CH}$=131, CHMe$_2$), 23.0 (q, $^1J_{CH}$=126, CHMe$_2$). Anal. Calcd for C$_{29}$H$_{43}$AlN$_2$Cl$_2$: C, 67.30; H, 8.76; N, 5.41. Found: C, 67.03; H, 8.39; N, 5.43.

Example 25

{$^t$BuC(NAr)$_2$}AlMe$_2$. This compound was prepared by the procedure described for {$^t$BuC(NAd)$_2$}AlMe$_2$, using 2.71 g 1,3-bis(2,6-diisopropylphenyl)carbodimide (7.48 mmol) in 80 mL Et$_2$O, 4.4 mL $^t$BuLi (1.7 M solution in pentane, 7.5 mmol) and 0.7 mL AlMe$_2$Cl (7.48 mmol) in 30 mL Et$_2$O. After 15 h the volatiles were removed under vacuum yielding an oily red-brown solid. {$^t$BuC(NAr)$_2$}AlMe$_2$ was extracted from LiCl with pentane and isolated from the extract by crystallization at -30° C. Yield 0.726 g, 20% based on AlMe$_2$Cl). $^1$H NMR (CD$_2$Cl$_2$): δ 7.18-7.12 (m, 6H, Ar), 3.45 (sept, $^3J_{HH}$=6.8, 4H, CHMe$_2$), 1.34 (d, $^3J_{HH}$=7.2, 12H, CHMe$_2$), 1.16 (d, $^3J_{HH}$=6.8, 12H, CHMe$_2$), 0.91 (s, 9H, CMe$_3$), -0.6 (s, 6H, AlMe$_2$). $^{13}$C NMR (CD$_2$Cl$_2$): δ 180.5 (s, CCMe$_3$), 145.0 (s, Ar—C$_{ortho}$), 139.6 (s, Ar—C$_{ipso}$), 125.9 (d, $^1J_{CH}$=161, Ar—C$_{para}$), 123.7 (d, $^1J_{CH}$=156, Ar—C$_{meta}$), 42.3 (s, CMe$_3$), 29.7 (q, $^1J_{CH}$= 127, CMe$_3$), 28.7 (d, J$_{CH}$=129, CHMe$_2$), 27.1 (q, $^1J_{CH}$=128, CHMe$_2$), 22.8 (q, $^1J_{CH}$=127, CHMe$_2$), -8.6 (br q, $^1J_{CH}$= 113.4, AlMe$_2$). Anal. Calcd for C$_{31}$H$_{49}$AlN$_2$: C, 78.10; H, 10.36; N, 5.88. Found: C, 77.61; H, 10.28; N, 5.78. The structure of this compound was confirmed by X-ray crystallography.

Example 26

[{$^t$BuC(N$^i$Pr)$_2$}Al$^i$Bu][B(C$_6$F$_5$)$_4$]. A solution of {$^t$BuC (N$^i$Pr)$_2$}Al$^i$Bu$_2$ (0.088 g, 0.27 mmol) in C$_6$D$_6$ (0.80 mL) was added to solid [Ph$_3$C][B(C$_6$F$_5$)$_4$] (0.250 g, 0.27 mmol) in a vial in the dry box. The mixture was transferred to an NMR tube and shaken vigorously for 2 min. Phase separation occurred to give a mixture of an orange oil (lower layer) and a pale yellow supernatent (upper layer). NMR spectra of the orange oily layer were recorded. These spectra established that the oil contains [{$^t$BuC(N$^i$Pr)$_2$}Al$^i$Bu][B(C$_6$F$_5$)$_4$], Ph$_3$CH and H$_2$C═CMe$_2$. $^1$H NMR (C$_6$D$_6$): δ 3.71 (br sept, $^1J_{HH}$=6.0, 2H, NCHMe$_2$), 1.39 (mult, 1H, CH$_2$CHMe$_2$), 1.03 (s, 9H, CMe$_3$), 0.78 (d, $^1J_{HH}$=5.8, 12H, NCHMe$_2$), 0.70 (d, $^1J_{HH}$=6.5, 6H, CH$_2$CHMe$_2$), -0.65 (d, $^1J_{HH}$=7.6, 2H, AlCH$_2$). $^{13}$C NMR (C$_6$D$_6$): δ 189.0 (s, CCMe$_3$), 46.0 (d, $^1J_{CH}$=140, NCHMe$_2$), 40.1 (s, CMe$_3$), 28.1 (q, $^1J_{CH}$=130, CH$_2$CHMe$_2$), 26.8 (q, $^1J_{CH}$=124, CMe$_3$), 25.2 (q, $^1J_{CH}$=128, NCHMe$_2$), 24.8 (d, $^1J_{CH}$=127, CH$_2$CHMe$_2$), 16.2 (br t, $^1J_{CH}$=118, AlCH$_2$).

Examples 27–31

Beta-diketiminato Complexes

Example 27

{HC(CMeNAr)$_2$}AlMe$_2$ (Ar=2,6-$^i$PrC$_6$H$_3$). A solution of AlMe$_3$ (0.108 g, 1.48 mmol) in hexanes (15 mL) was added to a rapidly stirred solution of HC(CMeNAr)$_2$H (0.600 g, 1.43 mmol) in hexanes (60 mL). A gas was evolved. After 15 h the volatiles were removed to afford {HC(CMeNAr)$_2$}AlMe$_2$ as a white crystalline solid (yield 0.569 g, 80%). Analytically pure samples were obtained as colorless crystals by recrystallization from a concentrated Et$_2$O solution at −30° C. $^1$H NMR (CD$_2$Cl$_2$): δ 7.23 (m, 6H, NAr), 5.20 (s, 1H, CH), 3.25 (sept, $^3J_{HH}$=6.8, 4H, CHMe$_2$), 1.77 (s, 6H, CMe), 1.25 (d, $^3J_{HH}$=5.8, 12H, CHMe$_2$), 1.17 (d, $^3J_{HH}$=7.6, 12H, CHMe$_2$), −0.99 (s, 6H, AlMe$_2$). $^{13}$C NMR (CD$_2$Cl$_2$): δ 170.1 (s, CMe), 144.7 (s, Ar—C$_{ortho}$), 141.1 (s, Ar—C$_{ipso}$), 126.9 (d, $^1J_{CH}$=161, Ar—C$_{para}$), 124.5 (d, $^1J_{CH}$=155, Ar—C$_{meta}$), 97.6 (d, $^1J_{CH}$=160, CH), 28.4 (d, $^1J_{CH}$=129, CHMe$_2$), 25.4 (q, $^1J_{CH}$=127, CHMe$_2$), 24.7 (q, $^1J_{CH}$=127, CHMe$_2$), 23.8 (q, $^1J_{CH}$=131, CMe), −10.6 (br q, $^1J_{CH}$=114, AlMe$_2$). Anal. Calcd for C$_{31}$H$_{47}$AlN$_2$: C, 78.44; H, 9.98; N, 5.90. Found: C, 78.58; H, 10.02; N, 5.81. The structure of this compound was confirmed by X-ray crystallography.

Example 28

{HC(CMeNAr)$_2$}Al$^i$Bu$_2$. This compound was prepared by the procedure described for {HC(CMeNAr)$_2$}AlMe$_2$ (Ar=2,6-$^i$PrC$_6$H$_3$), using 2.00 g HC(CMeNAr)$_2$H (4.78 mmol) in 50 mL pentane and 0.680 g Al$^i$Bu$_2$H (4.78 mmol) in 10 mL pentane. A gas was evolved. After 2.5 h the solution was concentrated to half volume. Pure {HC(CMeNAr)$_2$}Al$^i$Bu$_2$ was isolated from the solution by crystallization at −30° C. Yield 1.84 g (2 crops), 69%. $^1$H NMR (C$_6$D$_6$): δ 7.11 (m, 6H, NAr), 4.90 (s, 1H, CH), 3.46 (sept, $^3J_{HH}$=6.8, 4H, CHMe$_2$), 1.90 (m, $^3J_{HH}$=6.5, 2H, CH$_2$CHMe$_2$), 1.50 (s, 6H, CMe), 1.37 (d, $^3J_{HH}$=6.5, 12H, CHMe$_2$), 1.15 (d, $^3J_{HH}$=6.5, 12H, CHMe$_2$), 1.01 (d, $^3J_{HH}$=6.1, 12H, CHMe$_2$), 0.14 (d, $^3J_{HH}$=6.8, 4H, AlCH$_2$). $^{13}$C NMR (C$_6$D$_6$): δ 170.1 (s, CMe), 144.3 (s, Ar—C$_{ortho}$), 141.8 (s, Ar—C$_{ipso}$), 127.1 (d, $^1J_{CH}$=161, Ar—C$_{para}$), 124.5 (d, $^1J_{CH}$=157, Ar—C$_{meta}$), 99.1 (d, $^1J_{CH}$=159, CH), 28.8 (q, $^1J_{CH}$=124, CHMe$_2$), 28.0 (d, $^1J_{CH}$=127, CHMe$_2$), 27.1 (d, $^1J_{CH}$=123, CHMe$_2$), 25.5 (q, $^1J_{CH}$=126, CHMe$_2$), 24.9 (q, $^1J_{CH}$=126, CHMe$_2$), 23.8 (q, $^1J_{CH}$=122, CMe), 22.8 (br t, $^1J_{CH}$=109, AlCH$_2$).

Example 29

{HC(CMeNAr')$_2$}AlMe$_2$ (Ar'=2-$^t$BuC$_6$H$_4$). This compound was prepared by the procedure described for {HC(CMeNAr)$_2$}AlMe$_2$ (Ar=2,6-$^i$PrC$_6$H$_3$), using 0.501 g HC(CMeNAr')$_2$H (1.43 mmol) in 50 mL hexanes, and 0.103 g AlMe$_3$ (1.43 mmol) in 10 mL hexanes. A gas was evolved and the yellow solution became colorless after 1 h at room temperature. After a further 15 h the volatiles were removed to afford a yellow solid. Recrystallization from a concentrated Et$_2$O solution at −70° C. afforded pure {HC(CMeNAr')$_2$}AlMe$_2$ (0.274 g, 46%). $^1$H NMR (CD$_2$Cl$_2$): δ 7.53 (d, $^3J_{HH}$=6.8, 1H, Ar'), 7.53 (d, $^3J_{HH}$=7.9, 1H, Ar'), 7.22 (t, $^3J_{HH}$=7.2, 1H, Ar'), 7.21 (t, $^3J_{HH}$=7.4, 1H, Ar'), 7.18 (t, $^3J_{HH}$=7.0, 1H, Ar'), 7.17 (t, $^3J_{HH}$=7.0, 1H, Ar'), 6.92 (d, $^3J_{HH}$=7.2, 1H, Ar'), 6.91 (d, $^3J_{HH}$=6.8, 1H, Ar'), 5.06 (s, 1H, CH), 1.75 (s, 6H, CMe), 1.42 (s, 18H, CMe$_3$), −0.72 (s, 3H, AlMe), −1.12 (s, 3H, AlMe). $^{13}$C NMR (CD$_2$Cl$_2$): δ 170.8 (s, CMe), 144.4 (s, Ar'-C$_{ipso}$ or C$_{ortho}$), 144.0 (s, Ar'-C$_{ipso}$ or C$_{ortho}$), 130.1 (d, $^1J_{CH}$=153, Ar'), 129.4 (d, $^1J_{CH}$=158, Ar'), 126.9 (d, $^1J_{CH}$=160, Ar'), 126.5 (d, $^1J_{CH}$=159, Ar'), 97.1 (d, $^1J_{CH}$=160, CH), 36.7 (s, CMe$_3$), 32.9 (q, $^1J_{CH}$=126, CMe$_3$), 24.3 (q, J$_{CH}$=128, CMe), −8.36 (br q, $^1J_{CH}$=113, AlMe), −9.6 (br q, $^1J_{CH}$=113, AlMe). Anal. Calcd for C$_{27}$H$_{39}$AlN$_2$: C, 77.47; H, 9.39; N, 6.69. Found: C, 77.10; H, 9.17; N, 6.61. The structure of this compound was confirmed by X-ray crystallography.

Example 30

[{HC(CMeNAr)$_2$}Al$^i$Bu][B(C$_6$F$_5$)$_4$]. This compound was prepared by the procedure described for Example 26, using 0.103 g {HC(CMeNAr)$_2$}Al$^i$Bu$_2$ (0.18 mmol) and 0.171 g [Ph$_3$C][B(C$_6$F$_5$)$_4$] (0.19 mmol). The presence of [{HC(CMeNAr)$_2$}Al$^i$Bu][B(C$_6$F$_5$)$_4$] and Ph$_3$CH was confirmed by NMR spectroscopy. $^1$H NMR (C$_6$D$_6$): δ 6.95 (m, 4H, NAr),* 5.34 (s, 1H, CH), 2.44 (br sept, $^3J_{HH}$=6.8, 4H, CHMe$_2$), 1.51 (s, 6H, CMe), 1.12 (m, 1H, CH$_2$CHMe$_2$), 0.98 (d, $^3J_{HH}$=6.1, 24H, CHMe$_2$), 0.22 (d, $^3J_{HH}$=6.5, 6H, CH$_2$CHMe$_2$), 0.11 (d, $^3J_{HH}$=6.5, 2H, CH$_2$CHMe$_2$). $^{13}$C NMR (C$_6$D$_6$): δ 176.9 (s, CMe), 142.7 (s, Ar—C$_{ortho}$), 134.8 (s, Ar—C$_{ipso}$), 130.3 (d, $^1J_{CH}$=160, Ar—C$_{para}$), 125.6 (d, $^1J_{CH}$=161, Ar—C$_{meta}$), 104.0 (d, $^1J_{CH}$=168, CH), 29.8 (d, $^1J_{CH}$=127, CHMe$_2$), 26.6 (q, $^1J_{CH}$=125, CHMe$_2$), 24.2 (d, t, CHMe$_2$), 24.0 (q, $^1J_{CH}$=127, CHMe$_2$), 23.1 (q, $^1J_{CH}$=127, CHMe$_2$), 23.0 (q, $^1J_{CH}$=130, CMe), 17.2 (br t, $^1J_{CH}$=116, AlCH$_2$). * Remaining aromatic resonances obscured by overlap with Ph$_3$CH signals. † Splitting obscured by overlap.

Example 31

[{HC(C(MeNAr)$_2$}AlMe(NMe$_2$Ph)][B(C$_6$F$_5$)$_4$]. A CD$_2$Cl$_2$ solution (0.30 mL) of [HNMe$_2$Ph][B(C$_6$F$_5$)$_4$] (0.054 g, 0.067 mmol) was added to a vial containing a solution of {HC(CMeNAr)2}AlMe$_2$ (0.032 g, 0.067 mmol) in CD$_2$Cl$_2$ (0.30 mL). A gas was evolved. The solution was transferred to an NMR tube and NMR spectra were recorded. $^1$H NMR (CD$_2$Cl$_2$): δ 7.70 (m, 3H, NMe$_2$Ph+NAr), 7.54 (m, 2H, NMe$_2$Ph+NAr), 7.28 (m, 4H, NMe$_2$Ph+NAr), 7.21 (m, 2H, NMe$_2$Ph+NAr), 5.42 (s, 1H, CH), 3. 64 (s, 6H, NMe$_2$Ph), 3.45 (sept, $^1J_{HH}$=6.7, 2H, ChMe$_2$), 3.11 (sept, $^1J_{HH}$=6.8, 2H, CHMe$_2$), 1.86 (s, 6H, CMe), 1.30 (d, $^1J_{HH}$=6.8, 6H, CHMe$_2$), 1.25 (d, $^1J_{HH}$=7.2, 6H, CHMe$_2$), 1.22 (d, $^1J_{HH}$=6.5, 6H, CHMe$_2$), 1.10 (d, $^1J_{HH}$=6.8, 6H, CHMe$_2$), −1.01 (s, 3H, AlMe).

Examples 32–38

New Aluminum Guanidinate Complexes

Example 32

{Me$_2$NC(N$^i$Pr)$_2$}AlCl$_2$. A slurry of LiNMe$_2$ (0.765 g, 15.0 mmol) in Et$_2$O (25 mL) was cooled to 0° C., and a solution of 1,3-diisopropylcarbodiimide (1.89 g, 15.0 mmol) in Et$_2$O (15 mL) was added dropwise. The resulting mixture was allowed to warm to room temperature and stirred for 1 h. The mixture was cooled to −78° C. and a solution of AlCl$_3$ (2.00 g, 15.0 mmol) in Et$_2$O (15 mL) was added dropwise. The resulting mixture was allowed to warm to room temperature and stirred for 18 h. The volatiles were removed under vacuum and the product was extracted from the LiCl with toluene. The toluene extract was concentrated and cooled to −30° C. to yield clear, colorless crystals, which were isolated by filtration (2.20 g, 55% based on AlCl$_3$). $^1$H NMR (CD$_2$Cl$_2$) δ 3.56 (sept, $^3J_{HH}$=6.3, 2H, CHMe$_2$, 2.96 (s, 6H, NMe$_2$), 1.12 (d, $^{31}J_{HH}$=6.1, 12H, CHMe$_2$). $^{13}$C NMR (CD$_2$Cl$_2$) δ 169.1 (s, CN$_3$), 45.7 (d, $^1J_{CH}$=138, CHMe$_2$), 39.5 (q, $^1J_{CH}$=140, NMe$_2$), 23.9 (q, $^1J_{CH}$=125 CHMe$_2$). Anal. Calcd for C$_9$H$_{20}$AlCl$_2$N$_3$: C, 40.31; H, 7.52; N, 15.67. Found: C, 40.36; H, 7.74; N, 15.39. The structure of this compound was confirmed by X-ray crystallography.

Example 33

{Et$_2$NC(N$^i$Pr)$_2$}AlCl$_2$. This compound was prepared by the procedure outlined for {Me$_2$NC(N$^i$Pr)$_2$}AlCl$_2$, using 1.19 g of LiNEt$_2$ (15.0 mmol) 1.89 g of 1,3-diisopropylcarbodiimide (15.0 mmol), and 2.00 g of AlCl$_3$ (15.0 mmol). This complex was crystallized from toluene at −30° C. and isolated as clear, colorless crystals (3.01 g, 68% based on AlCl$_3$). $^1$H NMR (CD$_2$Cl$_2$) δ 3.46 (sept, 3J$_{HH}$=6.4, 2H, CHMe$_2$), 3.33 (q, $^3J_{HH}$=7.1, 4H, N(CH$_2$CH$_3$)$_2$), 1.19 (t, $^3J_{HH}$=6.7, 6H, N(CH$_2$CH$_3$)$_2$), 1.14 (d, $^3J_{HH}$=6.1, 12H, CHMe$_2$). $^{13}$C NMR (CD$_2$Cl$_2$): δ 168.8 (s, CN$_3$), 45.8 (d, $^1J_{CH}$=137, CHMe), 43.1 (t, $^1J_{CH}$=136, CH$_2$Me), 24.1 (q, $^1J_{CH}$=127, CHMe), 12.9 (q, $^1J_{CH}$=127, CH$_2$Me). Anal. Calcd for C$_{11}$H$_{24}$AlCl$_2$N$_3$: C, 44.60; H, 8.17; N, 14.19. Found: C, 44.58; H, 7.89; N, 14.04. MS (EI, m/z, $^{35}$Cl): 295 [M]$^+$, 280 [M—Me]$^+$.

Example 34

{Pr$_2$NC(N$^i$Pr)$_2$}AlCl$_2$. This compound was prepared by the procedure outlined for {Me$_2$NC(N$^i$Pr)$_2$}AlCl$_2$, using 1.61 g of LiN$^i$Pr$_2$ (15.0 mmol), 1.89 g of 1,3-diisopropylcarbodiimide (15.0 mmol), and 2.00 g of AlCl$_3$ (15.0 mmol). This complex was isolated as pale yellow crystals (1.134 g, 40.8% based on AlCl$_3$). $^1$H NMR (CD$_2$Cl$_2$) δ 3.77 (sept, $^3J_{HH}$=6.8, N(CHMe$_2$)2), 3.55 (sept, $^3J_{HH}$=6.2, NCHMe$_2$), 1.37 (d, $^3J_{HH}$=6.8, N(CHMe$_2$)$_2$), 1.18 (d, $^3J_{HH}$=5.8, NCHMe$_2$). $^{13}$C NMR (CD$_2$Cl$_2$): δ 172.5(s, CN$_3$), 51.1 (d, J$_{CH}$=136,CHMe$_2$), 45.9 (d, $^1J_{CH}$=135, CHMe$_2$), 24.7 (q, $^1J_{CH}$=125,CHMe$_2$), 23.5 (q, $^1J_{CH}$=125, CHMe$_2$). Anal. Calcd for C$_{13}$H$_{28}$AlCl$_2$N$_3$: C, 48.15; H, 8.70; N, 12.96. Found: C, 47.87, H, 8.68; N, 12.96. MS (EI, m/z, $^{35}$Cl): 295 [M]$^+$, 280 [M—Me]$^+$.

Example 35

{(Me$_3$Si)$_2$NC(N$^i$Pr)$_2$}AlCl$_2$. This compound was prepared by the procedure outlined for {Me$_2$NC(N$^i$Pr)$_2$}AlCl$_2$, using 2.00 g of LiN(SiMe$_3$)$_2$ (12.0 mmol), 1.51 g of 1,3-diisopropylcarbodiimide (12.0 mmol), and 1.59 g of AlCl$_3$ (12.0 mmol). The complex was extracted from the LiCl, recrystallized from pentane and isolated as white crystals (1.41 g, 40.8% based on AlCl$_3$). $^1$H NMR (CD$_2$Cl$_2$) δ 3.60 (sept, $^3J_{HH}$=6.6, 2H, CHMe$_2$), 1.14 (d, $^3J_{HH}$=6.5, 12H, CHMe$_2$), 0.30 (s, 18H, SiMe$_3$). $^{13}$C NMR (CD$_2$Cl$_2$) δ 172.4 (s, CN$_3$), 44.5 (d, $^1J_{CH}$=134, CHMe$_2$), 25.3 (q, $^1J_{CH}$=124, CHMe$_2$), 2.0 (q, $^1J_{CH}$=119, SiMe$_3$) Anal. Calcd for C$_{13}$H$_{32}$AlCl$_2$N$_3$Si$_2$: C, 40.61; H, 8.39; N, 10.63. Found: C, 40.44, H, 8.24; N, 10.72. MS(EI, m/z, $^{35}$Cl): 368 [M—Me]$^+$. The structure of this compound was confirmed by X-ray crystallography.

Example 36

{Me$_2$NC(N$^i$Pr)$_2$}AlMe$_2$. This compound was prepared by the procedure outlined for {Me$_2$NC(N$^i$Pr)$_2$}AlCl$_2$, using 0.809 g of LiNMe$_2$ (15.9 mmol), 2.00 g of 1,3-diisopropylcarbodiimide (15.9 mmol), and 1.47 mL of AlMe$_2$Cl (15.9 mmol). The complex was extracted from the LiCl with pentane. The volatiles were removed under vacuum to afford a sticky yellow solid. Clear, colorless crystals were obtained by sublimation at 60° C. onto a dry ice probe (0.30 g, 64.7% based on AlMe$_2$Cl). Note, because the complex is a liquid at room temperature a small aluminum pan was positioned beneath the cold probe of the sublimator to collect the sublimed product as it melted. $^1$H NMR (CD$_2$Cl$_2$): δ 3.50 (sept, $^3J_{HH}$=6.3, 2H, CHMe$_2$), 2.85 (s, 6H, NMe$_2$), 1.02 (d, J$_{HH}$=6.1, 12H, CHMe$_2$), −0.82 (s, 6H, AlMe$_2$). $^{13}$C NMR (CD$_2$Cl$_2$) δ 167.6 (s, CN$_3$), 45.2 (d, $^1J_{CH}$=135, CHMe$_2$), 39.2 (q, $^1J_{CH}$=136, NMe$_2$), 24.3 (q, $^1J_{CH}$=125, CHMe$_2$), −8.7 (q, $^1J_{CH}$=110 AlMe$_2$). Anal. Calcd for C$_{11}$H$_{26}$AlN$_3$: C, 58.12; H, 11.53; N, 18.48. Found: C, 57.97; H, 11.70; N, 18.25. MS (EI, m/z): 212 [M—Me]$^+$.

Example 37

{Et$_2$NC(N$^i$Pr)$_2$}AlMe$_2$. This compound was prepared by the procedure outlined for {Me$_2$NC(N$^i$Pr)$_2$}AlCl$_2$, using 1.25 g of LiNEt$_2$ (15.9 mmol), 2.00 g of 1,3-diisopropylcarbodiimide (15.9 mmol), and 1.47 mL of AlMe$_2$Cl (15.9 mmol). The product was extracted from the LiCl with pentane and the volatiles were removed under vacuum to afford a sticky orange solid, from which white crystals (2.39 g, 59% based on AlMe$_2$Cl) were isolated by sublimation at 60° C. onto a dry ice cooled probe. $^1$H NMR (CD$_2$Cl$_2$): δ 3.41 (sept, $^3J_{HH}$=6.3, 2H, CHMe$_2$), 3.21 (q, $^3J_{HH}$=7.3, 4H, N(CH$_2$CH$_3$)$_2$), 1.14 (t, $^3J_{HH}$=7.2, 6H, N(CH$_2$CH$_3$)$_2$), 1.03, (d, $^3J_{HH}$=6.5, 12H, CHMe$_2$), −0.82 (s, 6H, AlMe$_2$). $^{13}$C NMR (CD$_2$Cl$_2$) δ 167.3 (s, CN$_3$), 45.3 (d, $^1J_{CH}$=135, CHMe$_2$), 42.6 (t, $^1J_{CH}$=136, N(CH$_2$CH$_3$)$_2$), 24.6 (q, $^1J_{CH}$=126, CHMe$_2$), 13.2 (q, $^1J_{CH}$=126, N(CH$_2$CH$_3$)$_2$), −8.6 (q. $^1J_{CH}$=112, AlMe$_2$) Anal. Calcd for C$_{13}$H$_{30}$AlN$_3$: C, 61.14; H, 11.84; N, 16.45. Found: C, 60.88; H, 11.97; N, 16.30. MS (EI, m/z): 240 [M—Me]$^+$.

Example 38

{$^i$Pr$_2$NC(N$^i$Pr)$_2$}AlMe$_2$. This compound was prepared by the procedure outlined for {Me$_2$NC(N$^i$Pr)$_2$}AlCl$_2$, using 4.24 g of LiN$^i$Pr$_2$ (39.6 mmol), 5.00 g of 1,3-diisopropylcarbodiimide (39.6 mmol), and 3.68 mL of AlMe$_2$Cl (39.6 mmol). The product was extracted from the LiCl with pentane and the volatiles were removed under vacuum to afford a reddish-brown liquid from which white crystals were obtained by recrystallization from pentane in a −78° C. cold bath (5.26 g, 46.8% yield based on AlMe$_2$Cl). Analytically pure, waxy, white crystals were obtained by vacuum sublimation at 65° C. onto a dry ice probe (2.54 g, 22.6% yield based on AlMe$_2$Cl). The low final yield is due to the compound's high solubility in pentane. $^1$H NMR (CD$_2$Cl$_2$): δ 3.59 (sept, $^3J_{HH}$=5.7, 2H, N(CHMe$_2$)$_2$, 3.52 (sept, $^3J_{HH}$=6.0, 2H, NCHMe$_2$), 1.22 (d, $^3J_{HH}$=7.2, 12H, N(CHMe$_2$)$_2$), 1.04 (d, $^3J_{HH}$=6.1, 12H, NCHMe$_2$), −0.81 (s, 6H, AlMe$_2$). $^{13}$C NMR (CD$_2$C$_{12}$) δ 168.1 (s, CN$_3$), 49.1 (d, $^1J_{CH}$=132, N(CHMe$_2$)$_2$) 45.0 (d, $^1J_{CH}$=133, NCHMe$_2$), 25.5 (q, $^1J_{CH}$=125, N(CHMe$_2$)$_2$), 23.3 (q, $^1J_{CH}$=126, NCHMe$_2$), −9.4 (q, $^1J_{CH}$=115, AlMe$_2$).

Example 39

Ethylene Polymerization Using an Aluminum Guanidinate Catalyst

A solution of {$^i$Pr$_2$NC(N$^i$Pr)$_2$}AlMe$_2$ (120 mg, 0.423 mmol) in toluene was slowly added to a stirred solution of [Ph$_3$C][B(C$_6$F$_5$)$_4$] (390 mg, 0.423 mmol) in toluene. A red oil layer immediately appeared at the bottom of the flask.

The reaction mixture was stirred for 1 h and then was exposed to ethylene (1 atm). A white solid appeared immediately. The mixture was stirred 18 h and then was quenched with acidified methanol (50 mL). the polymer was collected by filtration, washed with 80 mL acidified water, and dried to yield 340 mg of polyethylene.

Examples 40–48

Gallium Amidinate Complexes

Example 40

${}^t$BuC(N${}^i$Pr)$_2$}GaCl$_2$. A colorless solution of GaCl3 (0.840 g, 4.75 mmol) in Et$_2$O (10 mL) was cooled to −78° C. and added dropwise to a slurry of Li[${}^t$BuC(N${}^i$Pr)$_2$] (0.904 g, 4.75 mmol) in Et$_2$O (40 mL), also at −78° C. The mixture was allowed to warm to room temperature and was stirred for 12 h affording a slurry of a white solid in a pale yellow solution. The mixture was filtered and the filtrate was concentrated to 30 mL and cooled at −78° C. to yield pure {${}^t$BuC(N${}^i$Pr)$_2$}GaCl$_2$ as colorless crystals that were collected by filtration (0.970 g, 64%). $^1$H NMR (C$_6$D$_6$): δ 3.82 (septet, $^3$J=6.5, 2H, CHMe$_2$), 1.14 (d, $^3$J=6.2, 12H, CHMe$_2$), 0.96 (s, 9H, CMe$_3$). $^{13}$C NMR (C$_6$D$_6$): δ 179.6, 47.5, 38.5, 28.6, 25.7. Anal. Calcd for C$_{11}$H$_{23}$Cl$_2$GaN$_2$: C, 40.78; H, 7.17; N, 8.65. Found: C, 40.45; H, 6.92; N, 8.57. EI-MS. (m/z): 324 [M]$^+$, 309 [M—CH$_3$]$^+$.

Example 41

{${}^t$BuC(NCy)$_2$}GaCl$_2$. The procedure described above for {${}^t$BuC(N${}^i$Pr)$_2$}GaCl$_2$ was followed using GaCl$_3$ (0.840 g, 4.75 mmol) and Li[${}^t$BuC(NCy)$_2$] (1.28 g, 4.75 mmol). Recrystallization from Et$_2$O yielded to pure {${}^t$BuC(NCy)$_2$}GaCl$_2$ as colorless crystals that were collected by filtration (1.21 g, 63%). $^1$H NMR (C$_6$D$_6$) : δ 3.58 (br m, 2H, Cy), 1.96 (br d, 4H, Cy), 1.64-1.42 (br m, 10H, Cy), 1.07 (s, 9H, CMe$_3$), 1.3-0.9 (br m, 6H, Cy). $^{13}$C NMR (C$_6$D$_6$): δ 179.8 (s, CCMe$_3$), 55.7 (d, $^1$J$_{CH}$=138, Cy—C$_1$), 38.6 (s, CMe$_3$), 36.9 (t, $^1$J$_{CH}$=128, Cy), 28.7 (q, $^1$J$_{CH}$=127, CMe$_3$), 25.4 (t, $^1$J$_{CH}$=127, Cy), 25.2 (t, $^1$J$_{CH}$=126, Cy). Anal. Calcd for C$_{17}$H$_{31}$Cl$_2$GaN$_2$: C, 50.52; H, 7.75; N, 6.93. Found: C, 50.41; H, 7.85; N, 6.93. EI-MS. (m/z): 404 [M]$^+$.

Example 42

{${}^t$BuC(N${}^i$Pr)$_2$}GaMe$_2$. {${}^t$BuC(N${}^i$Pr)$_2$}GaCl$_2$ was generated in situ in Et$_2$O (50 mL) as described above. The resulting mixture was cooled to −78° C. and 2 equiv of CH$_3$MgCl (6.34 mL of a 3.0 M solution in THF, 19.1 mmol) was added dropwise by syringe. The reaction mixture was allowed to warm to room temperature and was stirred for 15 h. The volatiles were removed under reduced pressure affording a pale yellow solid that was extracted with hexanes (70 mL). The extract was concentrated to 15 mL and cooled to −78° C. to yield pure {${}^t$BuC(N${}^i$Pr)$_2$}GaMe$_2$ as colorless crystals which were collected by filtration (1.36 g, 51%). $^1$H NMR (C$_6$D$_6$): δ 4.10 (septet, $^3$J=6.1, 2H, CHMe$_2$), 1.21 (s, 9H, CMe$_3$), 1.12 (d, $^3$J=6.1, 12H, CHMe$_2$), 0.24 (s, 6H, GaMe$_2$). $^{13}$C NMR (C$_6$D$_6$): δ 173.9 (s, CCMe$_3$), 46.3 (d, $^1$J$_{CH}$=139, CHMe$_2$), 39.3 (s, CMe$_3$), 29.6 (q, $^1$J$_{CH}$=127, CHMe$_2$), 26.2 (q, $^1$J$_{CH}$=125, CMe$_3$), −4.74 (q, $^1$J$_{CH}$=123, GaMe$_2$). Anal. Calcd for C$_{13}$H$_{29}$GaN$_2$: C, 55.14; H, 10.34; N,9.89. Found: C, 55.18; H, 10.44; N, 9.90. EI-MS. (m/z): 267 [M—CH$_3$]$^+$.

Example 43

{${}^t$BuC(NCy)$_2$}GaMe$_2$. {${}^t$BuC(NCy)$_2$}GaCl$_2$ was generated in situ in Et$_2$O (50 mL) as described above. The resulting mixture was cooled to −78° C. and CH$_3$MgCl (6.34 mL of a 3.0 M solution in THF, 19.1 mmol) was added dropwise by syringe. The reaction mixture was allowed to warm to room temperature and was stirred for 15 h. The volatiles were removed under reduced pressure affording a pale yellow solid that was extracted with hexanes (70 mL). The extract was concentrated to 15 mL and cooled to −78° C. to yield pure {${}^t$BuC(NCy)$_2$}GaMe$_2$ as large colorless crystals which were collected by filtration (1.81 g, 53%). $^1$H NMR (C$_6$D$_6$): δ 3.72 (br m, 2H, Cy), 2.00-1.95 (br d, 4H, Cy), 1.74-1.70 (br d, 4H, Cy), 1.61-1.57 (br d, 2H, Cy), 1.30-1.00 (br m, 10H, Cy), 1.29 (s, 9H, CMe$_3$), 0.26 (s, 6H, GaMe$_2$). $^{13}$C NMR (C$_6$D$_6$): δ 174.1 (s, CCMe$_3$), 55.0 (d, $^1$J$_{CH}$=128, Cy—C$_1$), 39.4 (s, CMe$_3$), 37.5 (t, $^1$J$_{CH}$=127, Cy), 29.7 (q, $^1$J$_{CH}$=122, CMe$_3$), 26.0 (t, $^1$J$_{CH}$=125, Cy), 25.9 (t, $^1$J$_{CH}$=125, Cy), −4.64 (q, $^1$J$_{CH}$=120, GaMe$_2$). Anal. Calcd for C$_{19}$H$_{37}$GaN$_2$: C, 62.81; H, 10.28, N 7.71. Found: C, H, N. EI-MS. (m/z): 348 [M]$^+$.

Example 44

{${}^t$BuC(N${}^i$Pr)$_2$}Ga(CH$_2$Ph)$_2$. {${}^t$BuC(N${}^i$Pr)$_2$}GaCl$_2$ was generated in situ in Et$_2$O (50 mL) as described above. The resulting mixture was cooled to −78° C. and PhCH$_2$MgCl (9.51 mL of a 1.0 M solution in Et$_2$O, 9.51 mmol) was added dropwise by syringe. The reaction mixture was allowed to warm to room temperature and was stirred for 15 h. The volatiles were removed under reduced pressure affording a pale yellow oil that was extracted with hexanes (70 mL). The extract was dried under vacuum for 12 h yielding pure {${}^t$BuC(N${}^i$Pr)$_2$}Ga(CH$_2$Ph)$_2$ as a colorless oil (1.36 g, 51%). $^1$H NMR (C$_6$D$_6$): δ 7.30-7.24 (m, 8H, o- and m-Ph), 7.1-7.0 (m, 2H, p-Ph), 3.90 (septet, $^3$J=5.8, 2H, CHMe$_2$), 2.35 (s, 4H, CH$_2$Ph), 1.14 (s, 9H, CMe$_3$), 0.88 (d, $^3$J=6.1, 12H, CHMe$_2$). $^{13}$C NMR (C$_6$D$_6$): δ 175.9 (s, CCMe$_3$), 145.4 (s, ipso-Ph), 128.4 (d, $^1$J$_{CH}$=160, o- or m-Ph), 127.9 (d, $^1$J$_{CH}$=155, o- or m-Ph), 122.6 (d, $^1$J$_{CH}$=165, p-Ph), 45.9 (d, $^1$J$_{CH}$=136, CHMe$_2$), 39.2 (s, CMe$_3$), 29.5 (q, $^1$J$_{CH}$=127, CHMe$_2$), 26.2 (q, $^1$J$_{CH}$=129, CMe$_3$), 23.6 (t, $^1$J$_{CH}$=123, CH$_2$Ph). Anal. Calcd for C$_{25}$H$_{37}$GaN$_2$: C, 68.97; H, 8.58; N 6.44. Found: C, 69.00; H, 8.68; N, 6.44. EI-MS. (EI, m/z): 434 [M]$^+$, 343 [M—C$_7$H$_9$]$^+$.

Example 45

{${}^t$BuC(N${}^t$Bu)$_2$}GaCl$_2$. A colorless solution of di-${}^t$Bu-carbodiimide (2.0 g, 13.0 mmol) in Et$_2$O (35 mL) was cooled to 0° C. and ${}^t$BuLi (7.62 mL of a 1.7 M solution in pentane, 13.0 mmol) was added dropwise by syringe. The reaction mixture was allowed to warm to room temperature and was stirred for 1 h resulting in a white slurry. A colorless solution of GaCl$_3$ (2.3 g, 13.0 mmol) in Et$_2$O (10 mL) cooled at −78° C. was added dropwise to the mixture also cooled at −78° C. The resulting mixture was allowed to warm to room temperature and was stirred for 12 h affording a slurry of a white solid in a pale yellow solution. The mixture was filtered and the filtrate was concentrated to 25 mL and cooled at −78° C. to yield pure {${}^t$BuC(N${}^t$Bu)$_2$}GaCl$_2$ as colorless crystals that were collected by filtration (0.71 g, 17%). $^1$H NMR (C$_6$D$_6$): δ 1.41 (s, 18H, N CMe$_3$), 1.13 (s, 9H, CMe$_3$). $^{13}$C NMR (C$_6$D$_6$): δ 183.7 (CCMe$_3$), 56.0 (NCMe$_3$), 37.3 (CCMe$_3$), 34.0 (NCMe$_3$), 31.2 (CCMe$_3$). Anal. Calcd for C$_{13}$H$_{27}$Cl$_2$GaN$_2$: C, 44.36; H, 7.75; N, 7.96. Found: C, 44.43; H, 7.82; N, 7.70. The structure of this compound was confirmed by X-ray crystallography.

Example 46

{${}^t$BuC(NCy)$_2$}Ga(CH$_2$Ph)$_2$. A colorless solution of {${}^t$BuC(NCy)$_2$}GaCl$_2$ (1.03 g, 2.55 mmol) in Et$_2$O (40 mL)

was cooled to −78° C. and PhCH$_2$MgCl (5.10 mL of a 1.0 M solution in Et$_2$O, 5.10 mmol) was added dropwise by syringe. The reaction mixture was allowed to warm to room temperature and was stirred for 15 h. The volatiles were removed under reduced pressure affording a pale yellow oil that was extracted with hexanes (70 mL). The extract was dried under vacuum for 12 h yielding pure {$^t$BuC(NCy)$_2$}Ga (CH$_2$Ph)$_2$ as a colorless oil (1.31 g, 70%). $^1$H NMR (C$_6$D$_6$): δ 7.33–7.26 (m, 8H, o- and m-Ph), 7.10–7.05 (m, 2H, p-Ph), 3.54 (m, 2H, Cy), 2.40 (s, 4H, CH$_2$Ph), 1.73–1.56 (m, 10H, Cy), 1.21 (s, CMe$_3$), 1.17–0.80 (m, 10H, Cy). $^{13}$C NMR (C$_6$D$_6$): δ 175.9 (s, CCMe$_3$), 145.6 (s, ipso-Ph), 128.4 (d, $^1J_{CH}$=158, o- or m-Ph), 128.0 (d, $^1J_{CH}$=156, o- or m-Ph), 122.7 (d, $^1J_{CH}$=155, p-Ph), 54.6 (d, $^1J_{CH}$=132, C$_1$—Cy), 39.2 (s, CMe$_3$), 37.2 (t, $^1J_{CH}$=127, Cy), 29.6 (q, $^1J_{CH}$=131, CMe$_3$), 25.8 (t, $^1J_{CH}$=125, Cy), 25.7 (t, $^1J_{CH}$=125, Cy), 23.8 (t, $^1J_{CH}$=124, CH$_2$Ph).

Example 47

{$^t$BuC(N$^i$Pr)$_2$}GaEt$_2$. {$^t$BuC(N$^i$Pr)$_2$}GaCl$_2$ (1a) was generated in situ in Et$_2$O (50 mL) as described above. The resulting mixture was cooled to −78° C. and of EtMgCl (9.51 mL of a 2.0 M solution in Et$_2$O, 19.1 mmol, 2 equiv) was added dropwise by syringe. The reaction mixture was allowed to warm to room temperature and was stirred for 15 h. The volatiles were removed under reduced pressure affording a pale yellow solid that was extracted with hexanes (70 mL). The extract was dried under vacuum for 12 h yielding pure {$^t$BuC(N$^i$Pr)$_2$}GaEt$_2$ as a colorless oil (1.72 g, 58%). $^1$H NMR (C$_6$D$_6$): δ 4.06 (septet, $^3J$=6.1, 2H, CHMe$_2$), 1.55 (t, $^3J$=7.9, 6H, GaCH$_2$CH$_3$), 1.23 (s, CMe$_{3,}$ 9H), 1.12 (d, $^3J$=6.5, CHMe$_2$, 12H), 0.85 (q, $^3J$=7.9, 4H, GaCH$_2$CH$_3$). $^{13}$C NMR (C$_6$D$_6$): δ 173.9 (s, CCMe$_3$), 46.3 (d, $^1J_{CH}$=139, CHMe$_2$), 39.3 (s, CMe$_3$), 29.6 (q, $^1J_{CH}$=127, CHMe$_2$), 26.2 (q, $^1J_{CH}$=125, CMe$_3$), −4.74 (q, $^1J_{CH}$=123, GaMe$_2$).

Example 48

[{$^t$BuC(N$^i$Pr)$_2$}Ga(CH$_2$Ph)][B(C$_6$F$_5$)$_4$]. C$_6$D$_6$ (0.5 mL) was vacuum transferred at −78° C. to a mixture of ($^t$BuC(N$^i$Pr)$_2$}Ga(CH$_2$Ph)$_2$ (84.0 mg, 0.193 mmol) and [Ph$_3$C][B(C$_6$F$_5$)$_4$] (178 mg, 0.193 mmol) in a resealable NMR tube. The tube was warmed to 23° C and vigorously shaken. The reaction mixture separated into two phases: a dark orange phase at the bottom of the tube and a light yellow phase on the top. After 15 min at 23° C., the bottom layer was analyzed by $^1$H NMR which indicated that [{$^t$BuC(N$^i$Pr)$_2$}Ga(CH$_2$Ph)][B(C$_6$F$_5$)$_4$] was the major species (70% NMR yield). $^1$H NMR (C$_6$D$_6$): δ 3.75 (septet, $^3J$=6.1 Hz, 2H, CHMe$_2$), 1.43 (s, 2H, GaCH$_2$Ph), 1.03 (s, 9H, CMe$_3$), 0.63 (d, $^3J$=6.1 Hz, 12H, CHMe$_2$).

Example 49–50

Ethylene Polymerizations By a Gallium Amidinate Catalyst

Example 49

A solution of {$^t$BuC(N$^i$Pr)$_2$}GaMe$_2$ (0.2 mmol) in toluene (20 mL) was prepared and 1 equiv. of B(C$_6$F$_5$)$_3$ was added. The mixture was put in a preheated oil bath at 50° C., charged with 4 atm of ethylene and vigorously stirred for 3 h. The mixture was allowed to cool to room temperature and quenched with 100 mL of methanol. The polymer was collected by filtration and dried under vacuum to afford 12 mg polyethylene.

Example 50

A solution of {$^t$BuC(N$^i$Pr)$_2$}Ga(CH$_2$Ph)$_2$ (0.2 mmole) in toluene (20 mL) was prepared and 1 equiv. of [Ph$_3$C][B(C$_6$F$_5$)$_4$] was added. The mixture was put in a preheated oil bath at 50° C., charged with 4 atm of ethylene and vigorously stirred for 3 h. The mixture was allowed to cool to room temperature and quenched with 100 mL of methanol. The polymer was collected by filtration and dried under vacuum to afford 65 mg polyethylene.

Examples 51–55

Aluminum Aminotroponiminate Complexes

Example 51

{($^i$Pr)$_2$ATI}Al(Et)$_2$. A hexane solution (ca. 20 mL) of {($^i$Pr)$_2$ATI}H (1.0 g, 4.9 mmol) was added to a solution of AlEt$_3$ (0.6 g, 5 mmol) in hexane at 0° C. The mixture was allowed to warm to 23° C. and stirred overnight. A small amount of insoluble solid was removed by filtration. The volatiles were removed under vacuum leaving a yellow solid. Recrystallization of this solid from pentane afforded {($^i$Pr)$_2$ATI}AlEt$_2$ as yellow powder (0.65 g, 46%). $^1$H NMR (C$_6$D$_6$): δ 6.75 (dd, $^3J_{HH}$=10.4, 10.4, 2H, H$_{4,6}$), 6.34 (d, $^3J_{HH}$=11.5, 2H, H$_{3,7}$), 6.21 (t, $^3J_{HH}$=9.4, 1H, H$_5$), 3.54 (sept, $^3J_{HH}$=6.5, 2H, NCHMe$_2$), 1.34 (t, $^3J_{HH}$=8.3, 6H, AlCH$_2$CH$_3$), 1.22 (d, $^3J_{HH}$=6.8, 12H, NCHMe$_2$), 0.38 (q, $^3J_{HH}$=7.9, 4H, AlCH$_2$CH$_3$). $^{13}$C NMR (C$_6$D$_6$): δ 161.6 (s, C$_{2,8}$), 136.5 (d, $^1J_{CH}$=153, C$_{4,6}$), 119.1 (d, $^1J_{CH}$=160, C$_{3,7}$), 113.7 (d, $^1J_{CH}$=151, C$_5$), 47.5 (d, $^1J_{CH}$=135, NCHMe$_2$), 22.2 (q, $^1J_{CH}$=125, NCHMe$_2$), 9.87 (q, $^1J_{CH}$=124, AlCH$_2$CH$_3$), 4.18 (t, $^1J_{CH}$=115, AlCH$_2$CH$_3$).

Example 52

{($^i$Pr)$_2$ATI}Al($^i$Bu)$_2$. A hexane solution (ca. 20 mL) of {($^i$Pr)$_2$ATI}H (1.17 g, 5.73 mmol) was added to a solution of Al($^i$Bu)$_3$ (1.27 g, 6.40 mmol) in hexane at 0° C. The mixture was allowed to warm to 23° C. and stirred overnight. A small amount of insoluble solid was removed by filtration. The volatiles were removed under vacuum leaving a yellow solid. Recrystallization of this solid from pentane afforded {($^i$Pr)$_2$ATI}Al($^i$Bu)$_2$ as yellow crystals (0.95 g, 48%). $^1$H NMR (C$_6$D$_6$): δ 6.76 (dd, $^3J_{HH}$=11.5, 9.0, 2H, H$_{4,6}$), 6.36 (d, $^3J_{HH}$=11.9, 2H, H$_{3,7}$), 6.20 (t, $^3J_{HH}$=9.0, 1H, H$_5$), 3.58 (sept, $^3J_{HH}$=6.5, 2H, NCHMe$_2$), 2.01 (nonet, $^3J_{HH}$=6.5, 2H, AlCH$_2$CHMe$_2$), 1.27 (d, $^3J_{HH}$=6.8, 12H, NCHMe$_2$), 1.12 (d, $^3J_{HH}$=6.1, 12H, AlCH$_2$CHMe$_2$), 0.38 (d, $^3J_{HH}$=6.8, 4HR, AlCH$_2$CHMe$_2$). $^{13}$C NMR (C$_6$D$_6$): δ 161.6 (s, C$_{2,8}$), 136.4 (d, $^1J_{CH}$=151, C$_{4,6}$), 119.2 (d, $^1J_{CH}$=158, C$_{3,7}$), 114.2 (d, $^1J_{CH}$=151, C$_5$), 47.5 (d, $^1J_{CH}$=135, NCHMe$_2$), 28.7 (q, $^1J_{CH}$=124, NCHMe$_2$), 27.3 (d, $^1J_{CH}$=124, AlCH$_2$CHMe$_2$), 26.5 (t, $^1J_{CH}$=107, AlCH$_2$CHMe$_2$), 22.3 (q, $^1J_{CH}$=126, AlCH$_2$CHMe$_2$). Anal. Calcd for C$_{21}$H$_{37}$N$_2$Al: C, 73.21; H, 10.82; N, 8.13. Found: C, 73.07; H, 11.04; N, 8.01.

Example 53

[{($^i$Pr)$_2$ATI}AlEt][B(C$_6$F$_5$)$_4$]. {($^i$Pr)$_2$ATI}AlEt$_2$ (0.104 g, 0.361 mmol) and [Ph$_3$C][B(C$_6$F$_5$)$_4$] (0.303 g, 0.328 mmol) were placed in a vial. Benzene (ca. 0.5 mL) was added and the mixture was stirred for 0.5 h. Hexane (ca. 5 mL) was added, the mixture was stirred and a yellow precipitate formed. The supernatant was removed using a pipette. The yellow solid was washed with hexane 4 times, collected by filtration and dried under vacuum affording [{($^i$Pr)$_2$ATI}AlEt][B(C$_6$F$_5$)$_4$] as yellow powder (226 mg, 74%). $^1$ NMR (ClC$_6$D$_5$): δ 6.91 (dd, $^3J_{HH}$=10.4, 10.4, 2H, H$_{4,6}$), 6.53 (t, $^3J_{HH}$=9.7, 1H, H$_5$), 6.49 (d, $^3J_{HH}$=11.2, 2H, H$_{3,7}$), 3.26 (sept, $^3J_{HH}$=6.5, 2H, NCHMe$_2$), 0.84 (d, $^3J_{HH}$=6.1, 12H, NCHMe$_2$), 0.79 (t, $^3J_{HH}$=8.3, 3H, AlCH$_2$CH$_3$), 0.19 (q, $^3J_{HH}$=6.5, 2H, AlCH$_2$CH$_3$). $^{13}$C NMR (C$_6$D$_6$, 50° C.): δ 159.6 (s, C$_{2,8}$), 149.1 (d, $^1J_{CF}$=240, B(C$_6$F$_5$)$_4^-$), 138.9 (d, $^1J_{CH}$=156, C$_{4,6}$), 138.8 (d, $^1J_{CF}$=245, B(C$_6$F$_5$)$_4^-$), 137.1 (d, $^1J_{CF}$=245, B(C$_6$F$_5$)$_4^-$), 129.5 (d, $^1J_{CH}$=161, C$_{3,7}$), 125.2 (br, ipso-B(C$_6$F$_5$)$_4^-$), 120.8 (d, $^1J_{CH}$=154, C$_5$), 47.2 (d, $^1J_{CH}$=138, NCHMe$_2$), 22.7 (q, $^1J_{CH}$=127, NCHMe$_2$), 7.06 (q, $^1J_{CH}$=128, AlCH$_2$CH$_3$), 3.24 (t, $^1J_{CH}$=120, AlCH$_2$CH$_3$). Anal. Calcd for C$_{39}$H$_{24}$AlBF$_{20}$N$_2$: C, 49.92; H, 2.58; N, 2.99. Found: C, 50.08; H, 2.73; N, 2.90.

Example 54

[{($^i$Pr)$_2$ATI}Al($^i$Bu)][B(C$_6$F$_5$)$_4$]. {($^i$Pr)$_2$ATI}Al($^i$Bu)$_2$ (0.141 g, 0.409 mmol) and [Ph$_3$C][B(C$_6$F$_5$)$_4$] (0.350 g, 0.379 mmol) were placed in a vial. Benzene (ca. 0.5 mL) was added and the mixture was stirred for 0.5 h. Hexane (ca. 5 mL) was added, the mixture was stirred and a yellow precipitate formed. The supernatant was removed by pipette. The yellow solid was washed with hexane 5 times, collected by filtration and dried under vacuum affording [{($^i$Pr)$_2$ATI}Al($^i$Bu)$_2$][B(C$_6$F$_5$)$_4$] as a yellow powder (244 mg, 67%). $^1$H NMR (C$_6$D$_6$, 60° C.): δ 7.23 (dd, $^3J_{HH}$=10.3, 10.1, 2H, H$_{4,6}$), 6.98 (d, $^3J_{HH}$=11.2, 2H, H$_{3,7}$), 6.86 (t, $^3J_{HH}$=9.4, 1H, H$_5$), 3.59 (sept, $^3J_{HH}$=6.5, 2H, NCHMe$_2$), 1.91 (nonet, $^3J_{HH}$=6.8, 2H, AlCH$_2$CHMe$_2$), 1.06 (d, $^3J_{HH}$=6.1, 12H, NCHMe$_2$), 0.93 (d, $^3J_{HH}$=6.5, 6H, AlCH$_2$CHMe$_2$), 0.64 (d, $^3J_{HH}$=7.6, 2H, AlCH$_2$CHMe$_2$). $^{13}$C NMR (C$_6$D$_6$, 50° C.): δ 159.6 (s, C$_{2,8}$), 149.1 (d, $^1J_{CF}$=242, B(C$_6$F$_5$)$_4^-$), 139.1 (d, $^1J_{CH}$=157, C$_{4,6}$), 138.8 (d, $^1J_{CF}$=246, B(C$_6$F$_5$)$_4^-$), 137.1 (d, $^1J_{CF}$=246, B(C$_6$F$_5$)$_4^-$), 129.8 (d, $^1J_{CH}$=158, C$_{3,7}$), 125.2 (br, ipso-B(C$_6$F$_5$)$_4^-$), 120.9 (d, $^1J_{CH}$=154, C$_5$), 47.3 (d, $^1J_{CH}$=138, NCHMe$_2$), 27.8 (q, $^1J_{CH}$=125, AlCH$_2$CHMe$_2$), 25.4 (d, $^1J_{CH}$=125, AlCH$_2$CHMe$_2$), 23.9 (t, $^1J_{CH}$=115, AlCH$_2$CHMe$_2$), 22.9 (q, $^1J_{CH}$=127, NCHMe$_2$). Anal. Calcd for C$_{41}$H$_{28}$AlBF$_2$ON$_2$: C, 50.95; H, 2.92; N, 2.90. Found: C, 51.04; H, 3.15; N, 2.92.

Example 55

Ethylene Polymerization by [{($^i$Pr)$_2$ATI}Al($^i$Bu)][B(C$_6$F$_5$)4]

Toluene (ca. 15 mL) was added to a mixture of {($^i$Pr)$_2$ATI}Al($^i$Bu)$_2$ (0.022 g, 0.064 mmol) and [Ph$_3$C][B(C$_6$F$_5$)$_4$] (0.066 g, 0.072 mmol). The mixture was stirred at 23° C. for 30 min and phase separation occurred. The mixture was degassed three times by the freeze/pump/thaw method. The mixture was heated to 80° C., 1 atm of ethylene was introduced and the reaction mixture was stirred for 1 h at 80° C. MeOH was added to the mixture and the resulting solid was collected by filtration, washed with MeOH and acetone, and dried under vacuum for 5 h affording 58 mg of polyethylene. Activity=908 gPE/mol●h●atm.

Example 56

Ethylene Polymerization by [{($^i$Pr)$_2$ATI}Al(Et)][B(C$_6$F$_5$)$_4$]

Toluene (ca. 15 mL) was added to a mixture of {($^i$Pr)$_2$ATI}Al(Et)$_2$ (0.015 g, 0.052 mmol) and [Ph$_3$C][B(C$_6$F$_5$)$_4$] (0.048 g, 0.052 mmol). The mixture was stirred at 23° C. for 30 min and phase separation occurred. The mixture was degassed three times by the freeze/pump/thaw method. The mixture was heated to 80° C., 1 atm of ethylene was introduced and the reaction mixture was stirred for 1 h at 80° C. MeOH was added to the mixture and the resulting solid was collected by filtration, washed with MeOH and acetone, and dried under vacuum for 5 h affording 136 mg of polyethylene. Activity=2615 gPE/mol●h●atm.

Example 57

Ethylene Polymerization by [{($^i$Pr)$_2$ATI}Al(Et)][B(C$_6$F$_5$)$_4$]

A suspension of [Ph$_3$C](B(C$_6$F$_5$)] (189 mg, 204 mmol) in toluene (36 mL) in a Fisher-Porter bottle was placed in a 100° C. oil bath, and stirred for 20 min. The [Ph$_3$C][B(C$_6$F$_5$)] dissolved. The solution was then degassed under vacuum, and ethylene (1 atm) was introduced. A solution of {$^i$Pr2ATI}AlEt$_2$ (59.0 mg, 204 mmol) in toluene (3 mL) was added by syringe. The ethylene pressure was increased to 5 atm, and the solution was stirred for 30 min. The ethylene was vented, the Fisher-Porter bottle was opened to air, and acidified methanol (75 mL) was added. The mixture stirred overnight. The polyethylene was isolated by filtration, washed with acidified water (15 mL, 5 times), rinsed with acetone, and dried under vacuum for 16 h. Yield of polyethylene: 555 mg; activity: 1080 gPE/mol*h*atm.

Example 58

Ethylene Polymerization by [{($^i$Pr)$_2$ATI}Al(Et)][B(C$_6$F$_5$)$_4$]

The procedure described in example 57 was repeated. Yield of polyethylene: 520 mg; activity: 1010 gPE/mol*h*atm.

Example 59

[({($^i$Pr)$_2$ATI}AlH)$_2$($\mu$-H)][B(C$_6$F$_5$)$_4$].{($^i$Pr)$_2$ATI}AlH$_2$ (0.070 g, 0.30 mmol) and [Ph$_3$C][B(C$_6$F$_5$)$_4$] (0.139 g, 0.151 mmol) were placed in an NMR tube. C$_6$D$_6$ (ca. 0.5 mL) was added by vacuum transfer at −78° C. Phase separation was observed in the NMR tube and NMR analyses were performed on the lower layer. The analyses indicated the presence of [{($^i$Pr)$_2$ATI}AlH]$_2$(□-H) [B(C$_6$F$_5$)$_4$] and Ph$_3$CH in the lower layer. $^1$H NMR (C$_6$D$_6$): □ 6.95 (dd, $^3J_{HH}$=10.4, 10.1, 4H, H$_{4,6}$), 6.53 (t, $^3J_{HH}$=9.5, 2H, H$_5$), 6.52 (d, $^3J_{HH}$=10.8, 4H, H$_{3,7}$), 4.54 (br, 3H, AlH), 3.28 (sept, $^3J_{HH}$ 6.1, 4H, NCHMe$_2$), 0.92 (d, $^3J_{HH}$=5.8, 24H, NCHMe$_2$). $^{13}$C NMR (C$_6$D$_6$): d 160.7 (s, C$_{2,8}$), 149.2 (d, $^1J_{CF}$=241, B(C$_6$F$_5$)$_4^-$), 138.9 (d, $^1J_{CF}$=248, B(C$_6$F$_5$)$_4^-$), 138.5 (d, $^1J_{CH}$=157, C$_{4,6}$), 137.1 (d, $^1J_{CF}$=259, B(C$_6$F$_5$)$_4^-$), 126.1 (d, $^1J_{CH}$=162, C$_{3,7}$), 125.2 (br, ipso-B(C$_6$F$_5$)$_4^-$), 118.3 (d, $^1J_{CH}$=153, C$_5$), 46.9 (d, $^1J_{CH}$=138, NCHMe$_2$), 22.4 (q, $^1J_{CH}$=127, NCHMe$_2$).

Resonances of Ph$_3$CH were also observed in the $^1$H {d□7.13-7.01 (m, 15H, Ph, 5.42 (s, 1H, Ph$_3$CH)} and $^{13}$C {d 144.4 (s, ipso-Ph), 129.9 (d, $^1J_{CH}$=158, o-Ph), 128.5 (d, $^1J_{CH}$=159, m-Ph), 126.4 (d, $^1J_{CH}$=160, p-Ph), 57.5 (d, $^1J_{CH}$=127, Ph$_3$CH)} NMR spectra.

Example 60

{MeC(NAd)S}AlMe. A suspension of adamantylisothiocyanate AdN═C═S (1.35 g, 7.00 mmol) in hexanes (50 mL) was added to a rapidly stirred solution of AlMe$_3$ (0.70 mL, 7.3 mmol) in hexanes (20 mL). The mixture was stirred at room temperature for 15 h to afford a slurry of a flocculent white precipitate in a yellow solution. The volatiles were removed under vacuum and {MeC(NAd)S}AlMe$_2$ was extracted with Et$_2$O (2×15 mL) and isolated from the extract by crystallization at −30° C. Yield 1.52 g, 78%. $^1$H NMR (CD$_2$Cl$_2$): δ 2.58 (s, 3H, CMe), 2.10 (br s, 3H, Ad—H$_g$), 1.95 (br d, $^2J_{HH}$=3.24, 6H, Ad—H$_b$), 1.71 (br d, $^1J_{HH}$=14.4, 3H, Ad—H$_d$), 1.67 (br d, $^1J_{HH}$=13.7, 3H, Ad—H$_d$), −0.58 (s, 6H, AlMe$_2$). $^{13}$C NMR (CD$_2$Cl$_2$): δ 196.0 (s, CMe), 58.9 (s, Ad—C$_a$), 42.3 (t, $^1J_{CH}$=127, Ad—C$_b$), 36.3 (t, $^1J_{CH}$=126, Ad—C$_d$), 29.9 (d, $^1J_{CH}$=133, Ad—C$_g$), 29.4 (q, $^1J_{CH}$=130, CMe), −8.8 (br q, AlMe$_2$). Anal. Calcd for C$_{14}$H$_{25}$AlNS: C, 63.12; H, 9.46; N, 5.26. Found: C, 63.32; H, 9.10; N, 5.11. The structure of this compound was confirmed by X-ray crystallography.

Example 61

{MeC(N$^t$Bu)})AlMe$_2$. A solution of AlMe$_3$ (1.04 g, 14.4 mmol) in hexanes (20 mL) was added to a rapidly stirred solution tert-butylisothiocyanate ($^t$BuN=C=S, 1.56 g, 14.0 mmol) in hexanes (80 mL). The solution was stirred for 2 h after which time a white precipitate and yellow solution had formed. Removal of the volatiles under vacuum afforded pure {MeC(N$^t$Bu)(S)}AlMe$_2$ as a yellow/orange liquid. Yield 2.32 g, 86%. $^1$H NMR (CD$_2$Cl$_2$): δ 2.54 (s, 3H, CMe), 1.35 (s, 9H, CMe$_3$), −0.59 (s, 6H, AlMe$_2$). $^{13}$C NMR (CD$_2$C$_{12}$): δ 196.2 (s, CMe), 57.7 (s, CMe$_3$), 29.7 (q, $^1J_{CH}$=126, CMe$_3$), 28.6 (q, $^1J_{CH}$=130, CMe), −9.2 (br q, $^1J_{CH}$=112, AlMe$_2$).

Example 62

{AdN(H)C(NAd)S}AlMe$_2$. A solution of AlMe$_3$ (0.210 g, 2.91 mmol) in hexanes (10 mL) was added to a suspension of bis(adamantyl)thiourea ((AdNH)$_2$C=S, 1.00 g, 2.90 mmol) in hexanes (80 mL). The solution became clear and a gas was evolved. After 15 h the volatiles were removed under vacuum to afford {AdN(H)C(NAd)(S)}AlMe$_2$ as a white solid (1.08 g, 93%). Analytically pure samples were obtained by recrystallization in Et$_2$O at 0° C. $^1$H NMR (CD$_2$Cl$_2$): δ 5.38 (s, 1H, NH), 2.14 (s, 6H, Ad), 2.10 (br d, 6H, Ad), 1.90 (br d, 6H, Ad), 1.69 (s, 6H, Ad), 1.70 (br d, 3H, Ad) , 1.64 (br d, 3H, Ad), −0.64 (s, 6H, AlMe$_2$). $^{13}$C NMR (CD$_2$Cl$_2$): δ 171.1 (s, CNHAd), 54.8 (s, Ad—Cα),* 42.7 (t, $^1J_{CH}$=129, Ad—Cβ), 42.4 (t, $^1J_{CH}$=127, Ad—Cβ), 36.6 (t, $^1J_{CH}$=127, Ad—Cδ), 36.5 (t, $^1J_{CH}$=128, Ad—Cδ), 30.2 (d, $^1J_{CH}$=133, Ad—Cγ), 29.9 (d, $^1J_{CH}$=128, Ad—Cγ), −7.7 (br q,$^1J_{CH}$=114, AlMe$_2$). * The two adamantyl Cα peaks are coincident at δ 54.8. Anal. Calcd for C$_{23}$H$_{37}$AlN$_2$S: C, 68.96; H, 9.31; N, 6.99. Found: C, 68.78; H, 9.30; N, 6.91. The structure of this compound was confirmed by X-ray crystallography.

Example 63

{ArN(E)C(NAr)S}AlMe$_2$. This compound was prepared by the procedure described for {AdN(H)C(NAd)S}AlMe$_2$, using 1.00 g bis(2,6-diisopropylphenyl)thiourea (2.52 mmol) in 80 mL pentane, and 0.186 g AlMe$_3$ (2.58 mmol) in 10 mL pentane. After 15 h the volatiles were removed under vacuum yielding {ArN(H)C(NAr)(S)}AlMe$_2$ as a white solid. Yield 0.946 g, 83% based on AlMe$_3$. $^1$H NMR (CD$_2$Cl$_2$): δ 7.36 (t, $^3J_{HH}$=7.9, 1H, Ar—H$_{para}$), 7.27 (m, 3H, Ar), 7.19 (d, $^3J_{HH}$=6.8, 2H, Ar—H$_{meta}$), 6.41 (br s, 1H, NH), 3.26 (sept, $^3J_{HH}$=6.7, 2H, CHMe$_2$), 3.06 (sept, $^3J_{HH}$=6.8, 2H, CHMe$_2$), 1.34 (d, $^3J_{HH}$=6.8, 6H, CHMe$_2$), 1.33 (d, $^3J_{HH}$=6.8, 6H, CHMe$_2$), 1.21 (d, $^3J_{HH}$=6.1, 6H, CHMe$_2$), 1.08 (d, $^3J_{HH}$=6.8, 6H, CHMe$_2$), −0.51 (s, 6H, AlMe$_2$). $^{13}$C NMR (CD$_2$Cl$_2$): δ 177.9 (s, CNHAr), 147.6 (s, Ar—C$_{ortho}$), 145.8 (s, Ar—C$_{ortho}$), 135.6 (s, Ar—C$_{ipso}$), 131.8 (s, Ar—C$_{ipso}$), 129.7 (d, $^1J_{CH}$=162, Ar—C$_{para}$), 128.0 (d, $^1J_{CH}$=160, Ar—C$_{para}$), 124.9 (d, $^1J_{CH}$=158, Ar—C$_{meta}$), 124.3 (d, $^1J_{CH}$=163, Ar—C$_{meta}$), 28.7 (d, $^1J_{CH}$=128, CHMe$_2$), 28.6 (d, $^1J_{CH}$=134, CHMe$_2$), 26.4 (q, $^1J_{CH}$=126, CHMe$_2$), 24.6 (q, $^1J_{CH}$=126, CHMe$_2$), 24.1 (q, $^1J_{CH}$=126, CHMe$_2$), 24.0 (q, $^1J_{CH}$=126, CHMe$_2$), −7.9 (q, $^1J_{CH}$=114, AlMe$_2$).

Example 64

{HC(CMeN$^t$Bu)(CMeO)}AlMe$_2$. This compound was prepared by the procedure described for {HC(CMeNAr)$_2$}AlMe$_2$ (Ar=2,6-$^i$PrC$_6$H$_3$), using 0.750 g HC(CMeN$^t$Bu)(CMeO)H (4.83 mmol) in 60 mL hexanes, and 0.348 g AlMe$_3$ (4.83 mmol) in 10 mL hexanes. After 16 h the volatiles were removed to afford a yellow solid. Recrystallization from a concentrated Et$_2$O solution at −70° C. afforded pure {HC(CMeN$^t$Bu)(CMeO)}AlMe$_2$ as a yellow crystalline solid. Yield 0.426 g, 42%. $^1$H NMR (C$_6$D$_6$): δ 4.57 (s, 1H, CH), 1.70 (s, 3H, CMe), 1.58 (s, 3H, CMe), 1.20 (s, 9H, CMe$_3$), −0.23 (s, 6H, AlMe$_2$). $^{13}$C NMR (C$_6$D$_6$): δ 177.2 (s, CMe), 175.5 (s, CMe), 101.3 (d, $^1J_{CH}$=158, CH), 57.1 (s, CMe$_3$), 31.3 (q, $^1J_{CH}$=126, CMe$_3$), 25.7 (q, $^1J_{CH}$=130, CMe), 24.9 (q, $^1J_{CH}$=127, CMe), −4.9 (br q, $^1J_{CH}$=107, AlMe$_2$). Anal. Calcd for C$_{11}$H$_{22}$AlNO: C, 62.53; H, 10.49; N, 6.63. The structure of this compound was confirmed by X-ray crystallography.

We claim:

1. A catalyst composition comprising three components, (1), (2) and (3), wherein:

Component (1) is a Lewis acid having the formula:

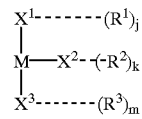

wherein
M is an atom selected from the group consisting of Group 13 elements in the oxidation state of (III);
X$^1$, X$^2$ and X$^3$ are the same or different and each is selected from the group consisting of hydrogen and the elements of Groups 14, 15, 16 and 17;
R$^1$, R$^2$ and R$^3$ are the same or different and each is selected from the group consisting of hydrogen, hydrocarbyl, a substituted hydrocarbyl, a nitrogen- or oxygen-containing heterocyclic, silyl, siloxy groups, and a metallic group, and two groups (R$^1$, R$^2$ or R$^3$) may be combined to form with X$^1$, X$^2$, or X$^3$ a cyclic group; and
j, k and m are the same or different and are 0, 1, 2 or 3 as required to satisfy the valence of each of atoms X$^1$, X$^2$ and X$^3$ to which R$^1$, R$^2$ and R$^3$, respectively, are bound;

Component (2) is a Lewis base having the formula E(R$^4$), wherein E is an atom selected from the group consisting of Group 15 and 16 elements; R$^4$ represents up to 3 substituents which are the same or different and are selected from the group consisting of hydrogen, hydrocarbyl, substituted hydrocarbyl, silyl, alkoxy, aryloxy and amino; n is 0, 1, 2 or 3 as required to satisfy the valence of E to which R$^4$ is bound; two R$^4$ substituents may be bonded together which with E form a cyclic group; and Component (2), E(R$^4$)$_n$, is utilized in the range of 0–1,000 molar equivalents relative to Component (1); and Component (3) is an activator selected from the group consisting of (a) a salt of a labile, weakly coordinating or non-coordinating anion that is capable of abstracting one of the —X$^1$—(R$^1$)$_j$, —X$^2$—(R$^2$)$_k$ or —X$^3$—(R$^3$)$_m$ groups from Component (1); (b) a neutral Lewis-acid that is capable of abstracting one of the —X—(R$^1$)$_j$, —X$^2$—(R$^2$)$_k$ or —X$^3$—(R$^3$) groups from Component (1); (c) an oxidizing agent capable of reacting with Component (1) and converting it to a cationic derivative; and (d) alumoxanes in a molar ratio of Components (1):(3) from 1:0.001–100,000.

2. A catalyst composition according to claim 1 wherein M is aluminum or gallium.

3. A catalyst composition according to claim 1 wherein M is aluminum.

4. A catalyst composition according to claim 1 wherein Components (1) and (2) constitute a Lewis-base complex of the Component (1) Lewis acid and the Component (2) Lewis base.

5. A catalyst composition according to claim 1 consisting essentially of Components (1) and (3).

6. A catalyst composition according to claim 2 wherein —X$^1$—(R$^1$)$_j$, —X$^2$—(R$^2$)$_k$ and —X$^3$—(R$^3$)$_m$ are the same or different and each represents hydrogen, alkyl of up to about 12 carbon atoms, bromide or chloride.

7. A catalyst composition according to claim 4 wherein Component (2) is selected from the group consisting of ethers, trialkylamines, pyridines, imines, anilines, phosphines and phosphites.

8. A catalyst composition according to claim 2 wherein Component (3) is selected from the group consisting of (a) salt selected from the group consisting of borate and aluminate salts; (b) a neutral Lewis-acid selected from the group consisting of boranes and alanes; (c) an oxidizing agent selected from the group consisting of ferrocenium and silver (I) salts of non-coordinating or weakly coordinating anions; and (d) methylalumoxane in a molar ratio to Component (1) within the range of 1:0.1–1,000.

9. A supported catalyst comprising Components (1), (2), and (3), as defined in claim 2, codeposited on a catalyst support material.

10. A supported catalyst according to claim 9 wherein the catalyst support material is selected from the group consisting of a polyolefin prepolymer, magnesium oxide, magnesium chloride, silica, alumina, and carbon.

11. A process for the preparation of a polymer of a polymerizable, unsaturated compound which comprises contacting a polymerizable, unsaturated compound with a catalyst composition defined in claim 1 under polymerization conditions of temperature and pressure.

12. A process according to claim 11 wherein the polymerizable, unsaturated compound comprises at least one α-olefin containing from 2 to 8 carbon atoms.

13. A process according to claim 11 wherein the polymerizable, unsaturated compound comprises ethylene.

14. A process according to claim 11 wherein the polymerization conditions comprise a temperature of 0 to 300° C. and a pressure of 1 to 1500 atmospheres.

15. A process according to claim 11 wherein the polymerization is carried out in a slurry mode of operation.

16. A process according to claim 11 wherein the polymerization is carried out in a solution mode of operation.

17. A process according to claim 11 wherein the polymerization is carried out in a bulk phase using either solution or slurry modes of operation.

18. A process according to claim 11 wherein the polymerization is carried out at a pressure in the range of 10 to 200 atmospheres.

19. A catalyst composition comprising two components, (3) and (4), wherein
Component (3) is an activator selected from the group consisting of (a) a salt of a labile, weakly coordinating or non-coordinating anion that is capable of abstracting one of the —X$^2$—(R$^2$)$_k$ or —X$^3$—(R$^3$)$_m$ groups from Component (4); (b) a neutral Lewis-acid that is capable of abstracting one of the —X$^2$—(R$^2$)$_k$ or —X$^3$—(R$^3$)$_m$ groups from Component (4); (c) an oxidizing agent capable of reacting with Component (4) and converting it to a cationic derivative; and (d) alumoxanes in a molar ratio of Components (4):(3) from 1:0.001–100,000; and Component (4) is a Group 13 metal complex having the formula:

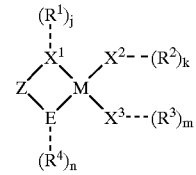

(II)

wherein
M is an atom selected from the group consisting of Group 13 elements in the oxidation state of (III);

$X^1$ is selected from the group consisting of elements of Groups 14, 15 and 16;

$X^2$ and $X^3$ are the same or different and each is selected from the group consisting of hydrogen and the elements of Groups 14, 15, 16 and 17;

E is an atom selected from the group consisting of Group 14, 15 and 16 elements;

$R^1$ are the same or different and each is selected from the group consisting of hydrogen, hydrocarbyl, substituted hydrocarbyl, a nitrogen- or oxygen-containing heterocyclic, alkoxy, amino, and silyl groups, and two groups ($R^1$) may be combined to form with $X^1$ a cyclic group;

$R^2$ and $R^3$ are the same or different and each is selected from the group consisting of hydrogen, hydrocarbyl, substituted hydrocarbyl, a nitrogen- or oxygen-containing heterocyclic group, silyl, alkoxy, amino, siloxy and a metallic group and two groups ($R^2$ or $R^3$) may be combined to form with $X^2$ or $X^3$ a cyclic group;

$R^4$ represent up to 3 substituents which are the same or different and are selected from the group consisting of hydrogen, hydrocarbyl, substituted hydrocarbyl, a nitrogen- or oxygen-containing heterocyclic, silyl, alkoxy, aryloxy and amino groups and two $R^4$ groups may be combined to form with E a cyclic group;

j, k, m and n are the same or different and are 0, 1, 2 or 3 as required to satisfy the valence of each of atoms $X^1$, $X^2$, $X^3$ and E to which $R^1$, $R^2$, $R^3$, and $R^4$, respectively, are bound; and Z if present is a saturated or unsaturated linking group or if Z is not present, $X^1$ and E are not directly bonded to each other.

20. A catalyst composition according to claim 19 wherein M of Component (4) is selected from the group consisting of aluminum and gallium.

21. A catalyst composition according to claim 19 wherein M of Component (4) is aluminum.

22. A catalyst composition according to claim 20 wherein Z of Component (4), if present, is selected from the group consisting of unsaturated linking groups having the structures:

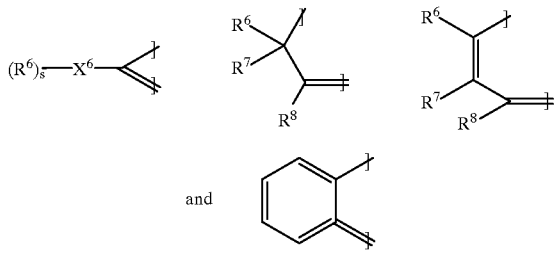

wherein R⁶, R⁷ and R⁸ are the same or different and each is selected from the group consisting of hydrogen, hydrocarbyl, substituted hydrocarbyl, and silyl groups with 1 to about 30 carbon atoms; $X^6$ is an oxygen, nitrogen, carbon or silicon atom; s is 1, 2, or 3 as required to satisfy the valence of $X^6$; and any two groups (R⁶, R⁷ and R⁸) may be combined to form with $X^1$, $X^6$ or E a cyclic group.

23. A catalyst composition according to claim 20 wherein $X^1$ and E of Component (4) are nitrogen atoms.

24. A catalyst composition according to claim 23 wherein $R^1$ and $R^4$ are independently selected from the group consisting of hydrocarbyl, substituted hydrocarbyl, and silyl groups of 1 to about 30 carbon atoms; and j and n each is 1.

25. A catalyst composition according to claim 24 in which Component (4) has the formula:

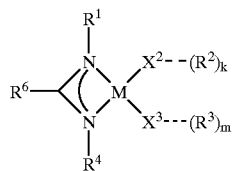

wherein $R^6$ is selected from the group consisting of a hydrocarbyl, substituted hydrocarbyl or a silyl group containing less than 30 carbon atoms.

26. A catalyst composition according to claim 24 in which Component (4) has the formula:

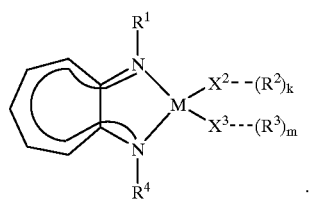

27. A catalyst composition according to claim 24 in which Component (4) has the formula:

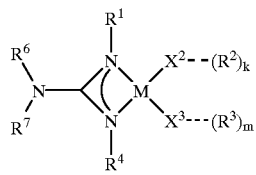

wherein R⁶ and R⁷ are the same or different and each is selected from the group consisting of hydrogen, hydrocarbyl, substituted hydrocarbyl, and silyl groups with 1 to about 30 carbon atoms and the groups $R^1$, $R^4$, $R^6$ and $R^7$ may be combined so as to form cyclic groups.

28. A catalyst composition according to claim 20 wherein —$X^2$—$(R^2)_k$ and —$X^3$—$(R^3)_m$ represent hydrogen, hydrocarbyl, or halogen.

29. A catalyst composition according to claim 28 wherein —$X^2$—$(R^2)_k$ and —$X^3$—$(R^3)_m$ represent alkyls of up to about 12 carbon atoms, bromide or chloride.

30. A catalyst composition according to claim 20 wherein Component (3) is selected from the group consisting of (a) a salt selected from the group consisting of borate and aluminate salts; (b) a neutral Lewis-acid selected from the group consisting of boranes and alanes; (c) an oxidizing agent selected from the group consisting of ferrocenium and silver (I) salts of non-coordinating or weakly coordinating anions; and (d) methylalumoxane in a molar ratio of Components (4):(3) from 1:0.1–1,000.

31. A supported catalyst comprising Components (3) and (4), as defined in claim 19, codeposited on a catalyst support material.

32. A supported catalyst according to claim 31 wherein the catalyst support material is selected from the group consisting of a polyolefin prepolymer, magnesium oxide, magnesium chloride, silica, alumina, and carbon.

33. A process for the preparation of a polymer of a polymerizable, unsaturated compound which comprises contacting a polymerizable, unsaturated compound with a catalyst composition defined in claim 20 under polymerization conditions of temperature and pressure.

34. A process according to claim 33 wherein the polymerizable, unsaturated compound comprises at least one α-olefin containing from 2 to 8 carbon atoms.

35. A process according to claim 33 wherein the polymerizable, unsaturated compound comprises ethylene.

36. A process according to claim 33 wherein the polymerization conditions comprise a temperature of 0 to 300° C. and a pressure of 1 to 1500 atmospheres.

37. A process according to claim 33 wherein the polymerization is carried out in a slurry mode of operation.

38. A process according to claim 33 wherein the polymerization is carried out in a solution mode of operation.

39. A process according to claim 33 wherein the polymerization is carried out in a bulk phase using either solution or slurry modes of operation.

40. A process according to claim 33 wherein the polymerization is carried out at a pressure in the range of 10 to 200 atmospheres.

41. A supported catalyst comprising a cationic Group 13 complex compound (5) deposited on a catalyst support material, wherein the cationic Group 13 complex compound (5) has the formula

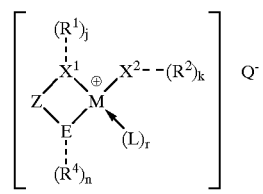

(III)

wherein

M is an atom selected from the group consisting of aluminum and gallium;

$X^1$ is selected from the group consisting of elements of Groups 14, 15 and 16;

$X^2$ is selected from the group consisting of the elements of Groups 14, 15, 16 and 17;

E is an atom selected from the group consisting of the Group 14, 15 and 16 elements;

$R^1$ are the same or different and each is selected from the group consisting of hydrogen, hydrocarbyl, substituted hydrocarbyl, a nitrogen- or oxygen-containing heterocylic, alkoxy, amino, and silyl groups, and two groups ($R^1$) may be combined to form with $X^1$ a cyclic group;

$R^2$ are the same or different and each is selected from the group consisting of hydrogen, hydrocarbyl, substituted hydrocarbyl, a nitrogen- or oxygen-containing heterocyclic, silyl, alkoxy amino, siloxy groups and a metallic group and two groups ($R^2$) may be combined to form with $X^2$ a cyclic group;

$R^4$ represent up to 3 substituents which are the same or different and are selected from the group consisting of hydrogen, hydrocarbyl substituted hydrocarbyl, nitrogen- or oxygen-containing heterocyclic, silyl, alkoxy, and amino groups and two groups ($R^4$) may be combined to form with E a cyclic group;

j, k, and n are the same or different and are 0, 1, 2 or 3 as required to satisfy the valence of each of atoms $X^1$, $X^2$, and E to which $R^1$, $R^2$, and $R^4$, respectively, are bound;

r is 0–3;

Z if present is a saturated or unsaturated linking group or if Z is not present, $X^2$ and E are not directly bonded to each other;

L if present is a neutral Lewis base, donor ligand or a neutral or cationic Group 13 metal species which coordinates through a bridging group; and Q is a non-coordinating or weakly coordinating anionic group.

42. A supported catalyst according to claim 41 wherein the catalyst support material is a polyolefin prepolymer, magnesium oxide, magnesium chloride, silica, alumina or carbon.

* * * * *

UNITED STATES PATENT AND TRADEMARK OFFICE
CERTIFICATE OF CORRECTION

| | | |
|---|---|---|
| PATENT NO. | : 6,228,794 B1 | Page 1 of 1 |
| DATED | : May 8, 2001 | |
| INVENTOR(S) | : Richard F. Jordan, Martyn P. Coles, Samuel Dagorne, and Eiji Ihar | |

It is certified that error appears in the above-identified patent and that said Letters Patent is hereby corrected as shown below:

<u>Column 1,</u>
After title, please insert:
GRANT REFERENCE

-- Work for this invention was funded by a grant from the National Science Foundation. Grant No. NSF CHE94-13022(003). The Government may have certain righs in this invention. --

Signed and Sealed this

Twelfth Day of March, 2002

Attest:

*Attesting Officer*

JAMES E. ROGAN
*Director of the United States Patent and Trademark Office*